(12) United States Patent
Malfroy-Camine et al.

(10) Patent No.: US 7,122,537 B2
(45) Date of Patent: *Oct. 17, 2006

(54) CYCLIC SALEN-METAL COMPOUNDS AS SCAVENGERS FOR OXYGEN RADICALS AND USEFUL AS ANTIOXIDANTS IN THE TREATMENT AND PREVENTION OF DISEASES

(75) Inventors: Bernard Malfroy-Camine, Arlington, MA (US); Susan Robin Doctrow, Roslindale, MA (US)

(73) Assignee: Eukarion, Inc., Woburn, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/432,752

(22) PCT Filed: Nov. 28, 2001

(86) PCT No.: PCT/US01/44686

§ 371 (c)(1),
(2), (4) Date: May 27, 2003

(87) PCT Pub. No.: WO02/44187

PCT Pub. Date: Jun. 6, 2002

(65) Prior Publication Data

US 2004/0059107 A1 Mar. 25, 2004

(51) Int. Cl.
*C07D 273/08* (2006.01)
*A61K 31/555* (2006.01)
*A61K 31/28* (2006.01)

(52) U.S. Cl. ............ 514/185; 514/450; 540/541; 540/465; 556/32; 556/45

(58) Field of Classification Search ............ 514/185, 514/450; 540/541, 465; 556/32, 45
See application file for complete search history.

(56) References Cited

U.S. PATENT DOCUMENTS

| 5,106,841 | A | 4/1992 | Scheer |
| 5,223,538 | A | 6/1993 | Fridovich et al. |
| 5,403,834 | A | 4/1995 | Malfroy-Camine et al. |
| 5,696,109 | A | 12/1997 | Malfroy-Camine et al. |
| 5,827,880 | A | 10/1998 | Malfroy-Camine et al. |
| 5,834,509 | A | 11/1998 | Malfroy-Camine et al. |
| 6,046,188 | A | 4/2000 | Malfroy-Camine |
| 6,589,948 | B1 * | 7/2003 | Malfroy-Camine et al. . 514/185 |

FOREIGN PATENT DOCUMENTS

| WO | WO 93/03838 | 3/1993 |
| WO | WO 96/40148 A1 | 12/1996 |
| WO | WO 96/40149 A1 | 12/1996 |

OTHER PUBLICATIONS

Aguiari, et al., *Inorganica Chimica Acta*, 219:135-146 (1994).
Baudry, et al., *Biochemical and Biophysical Research Communications*, 192(2):964-968 (1993).
Beckman, et al., *Proc. Natl. Acad. Sci. (U.S.A.)*, 87:1620 (1990).
Boucher, *J. Inorg. Nucl. Chem.*, 36:531-536 (1974).
Breimer, *Brit J. Cancer*, 57:6 (1988).
Bruce, et al., *Abstr. Soc. Neurosci.*, 19:1680 (1993).
Cadenas, *Ann. Rev. Biochem.*, 58:79 (1989).
Canfield, et al., *Proc. Soc. Exp. Biol. Med.*, 200:260 (1992).
Coleman, et al., *Inorg. Chem.*, 20:1253-1258 (1981).
Czapski, et al., "Superoxide Scavengers and Sod or Sod Mimics," in *Antioxidants in Therapy and Preventive Medicine*, Eds. Emerit, et al., Plenum Press, New York, pp. 45-50.
de Garavilla, et al., *Drug Development Research*, 25:139-148 (1992).
Foye, "Radioprotective Drugs," in *Burger's Medicinal Chemistry*, Fourth Edition, Part III, pp. 11, 22, 29-35, 39, 44 (1981).
Fu, et al., *J. Org. Chem.*, 56:6497 (1991).
Fu, et al., *J. Organic Chem.*, 113:6703-6704.
Grubbs, et al., *Acc. Chem. Res.*, 28:446-452 (1995).
Gutteridge, et al., *Arch. Biochem. Biophys.*, 283:223 (1990).
Ito, et al., *Chemical Abstracts*, vol. 111, Abstract No. 153260 (1989).
Jacobsen, et al., *J. Amer. Chem. Soc.*, 113:7063-7064 (1991).
Jacobsen, et al., *J. Organic Chem.*, 113:6703-6704 (1991).
Jacobsen, National Institute of General Medical Sciences Notice of Grant Award, Grant No. 1 R01 GM 43214-01A1 (1991).
Jacobsen, National Science Foundation, Presidential Young Investigator Award, Grant No. CHE-9057740 (1990).
Kensler, et al., *Science*, 221:75-77 (1983).
Kessel, et al., *Inorg. Chem.*, 19:1170-1178 (1980).
Krinsky, *Proc. Soc. Exp. Biol. Med.*, 200:248-254 (1992).
Kroll, et al., *Chem. Commun.*, 839:1971).
Lee, et al., *Tetrahedron Letters*, 32(38):5055-5058 (1991).
Lee, et al., *Tetrahedron Letters*, 32(45):6533-6536 (1991).
Marletta, *Trends Biochem. Sci.*, 14:488 (1989).
Matsushita, et al., *Bull. Chem. Sco. Jpn.*, 54:2646-2651 (1981).
Matsushita, et al., *Bull. Chem. Soc. Jpn.*, 54:3743-3748 (1981).
Matsushita, et al., *Chemical Abstracts*, vol. 96, Abstract No. 114881 (1981).
Miyaura, et al., *Tetrahedron Lett.*, 22:127 (1981).
Moncada, et al., *Biochem. Pharmacol.*, 38:1709 (1989).
Nagano, et al., *J. Biol. Chem.*, 264(16)9243-9249 (1989).

(Continued)

*Primary Examiner*—Kahsay Habte
(74) *Attorney, Agent, or Firm*—Carol L. Francis; Edward J. Baba; Bozicevic, Field & Francis LLP

(57) ABSTRACT

This invention provides antioxidant cyclic salen-metal compounds, compositions of such antioxidant cyclic salen-metal compounds having superoxide activity, catalase activity and/or peroxidase activity and methods of using such antioxidant cyclic salen-metal compositions to treat or prevent a disease associated with cell or tissue damage produced by free radicals, such as superoxide.

26 Claims, 12 Drawing Sheets

OTHER PUBLICATIONS

Pasini, et al., "Optically Active Complexes of Schiff Bases. Part 4. An Analysis of the Circular-dichroism Spectra of some Complexes of Different Co-ordination Numbers with Quadridentale Schiff Bases of Optically Active Diamines," J.C.S. Dalton, pp. 346-356.

Pryor, *Free Radicals in Biol.* 11:1 (1976).

Saran, et al., *Free Rad. Res. Commun.*, 10:221 (1990).

Sittig, *Handbook of Toxic and Hazardous Chemicals and Carcinogens*, pp. 559-562, 639-641, 243-248 (1985).

Stadtman, *Science*, 257:1220 (1992).

Yamamoto, et al., *Carcinogenesis*, 11(5)749-754 (1990).

Zhang, et al., *J. Am. Chem. Soc.*, 112:2801-2803.

Zhang, et al., *J. Am. Chem. Soc.*, 56:2296-2298.

Zimmerman, *Chest*, 100:189S (1991).

* cited by examiner

C101:

C102:

C103:

C104:

C105:
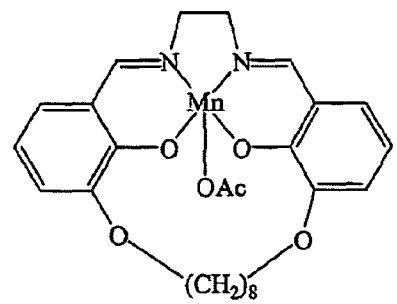
C106:
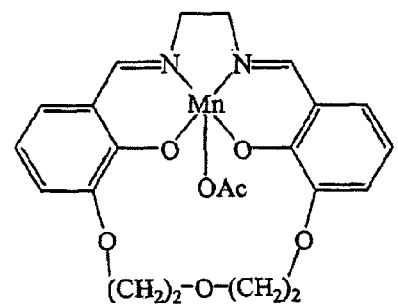
C107:
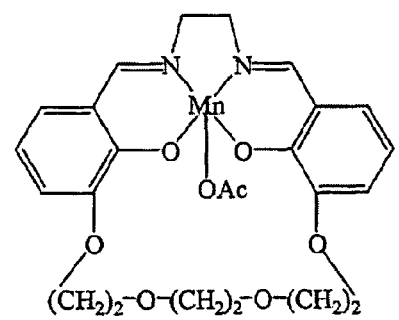
C108:
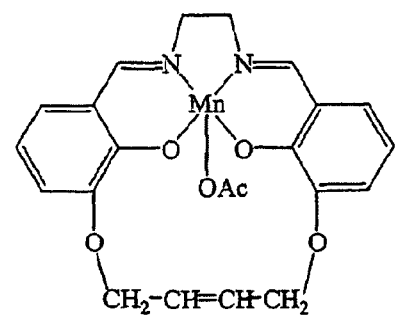
*FIG. 1 CON'T*

C109:
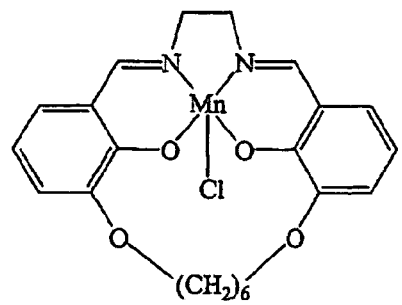
C110:
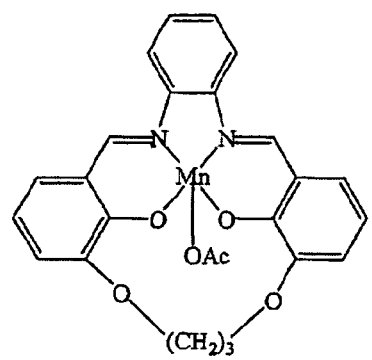
C111:
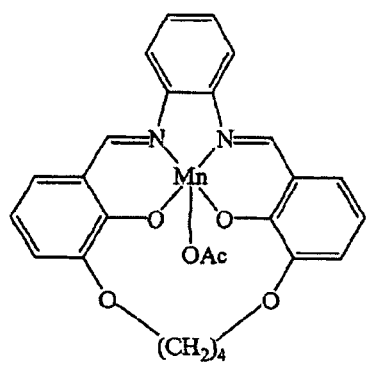
*FIG. 1 CON'T*

C112:
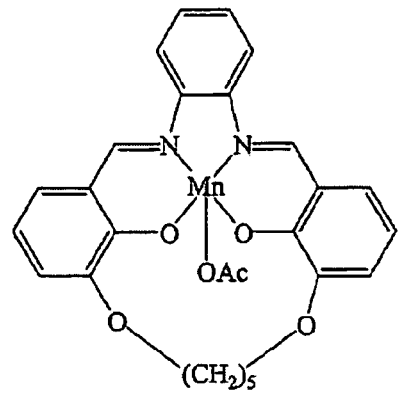
C113:
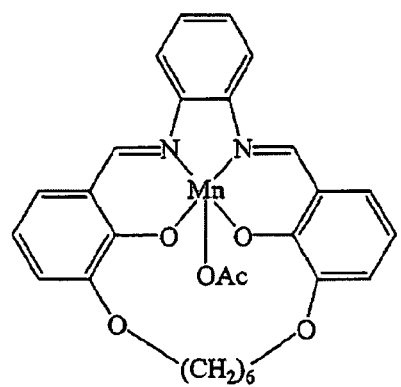
C114:
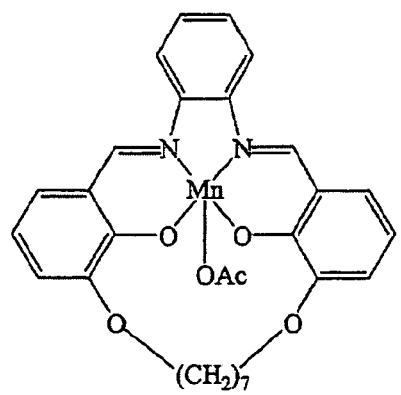
*FIG. 1 CON'T*

C115:
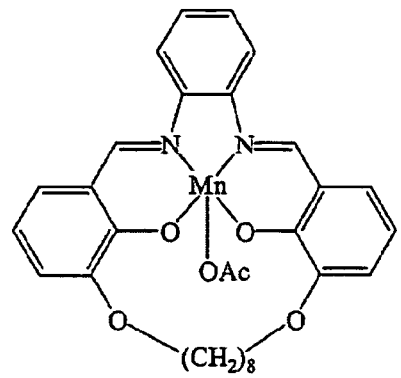
C116:
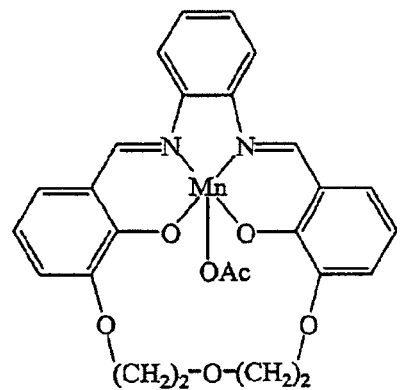
C117:
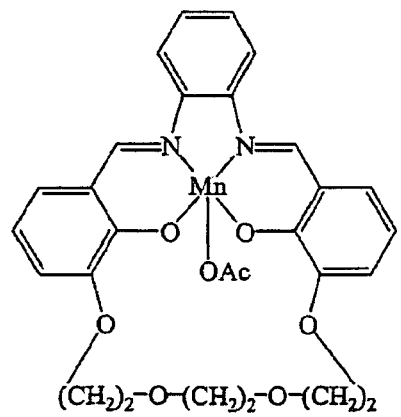
*FIG. 1 CON'T*

C118:
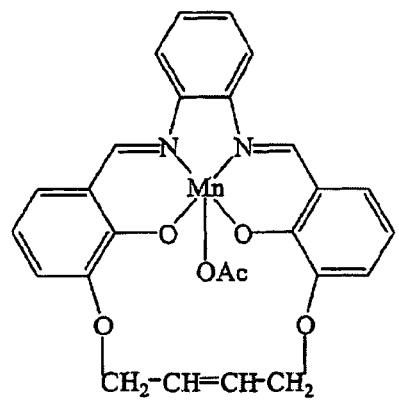
C119:
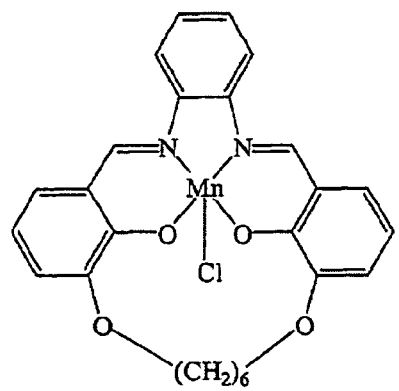
C120:
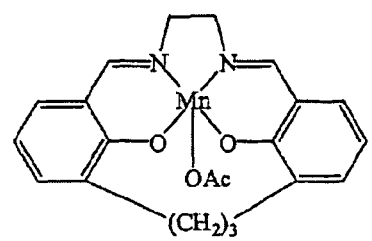
C121:
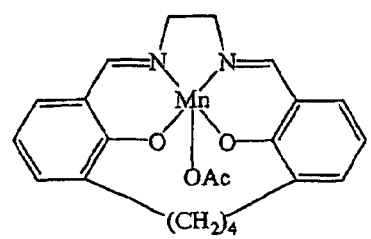
*FIG. 1 CON'T*

C122:
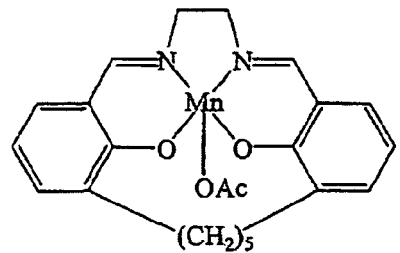
C123:
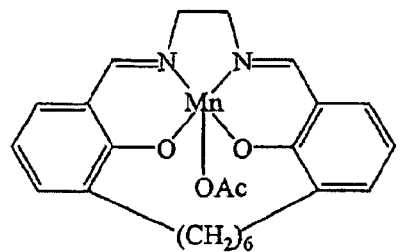
C124:
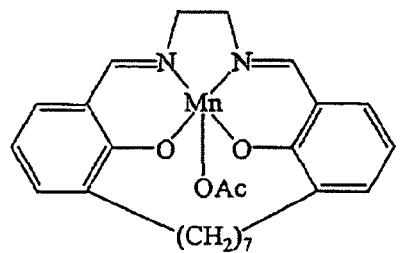
C125:
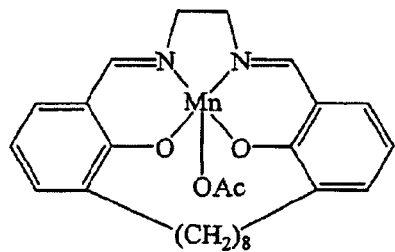
C126:
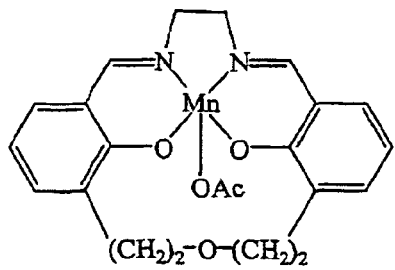
*FIG. 1 CON'T*

C127:
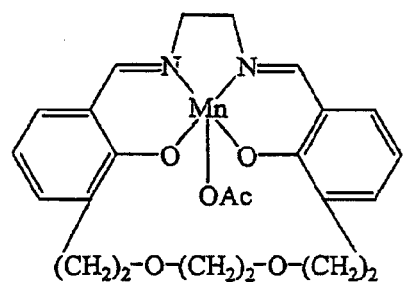
C128:
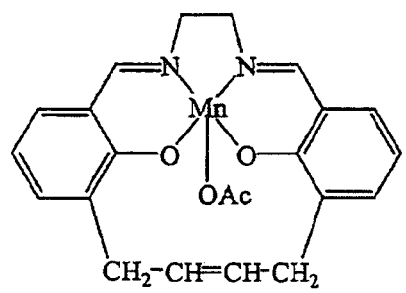
C129:
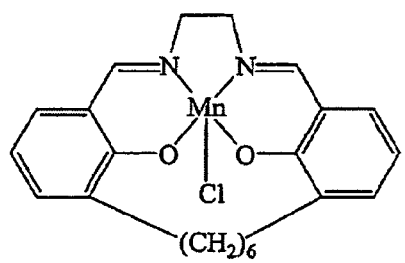
C130:
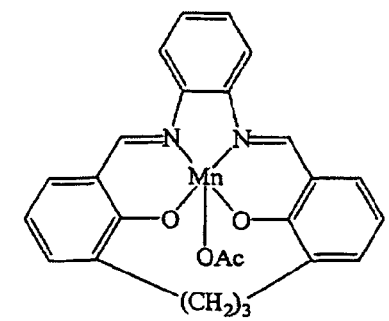
*FIG. 1 CON'T*

C131:
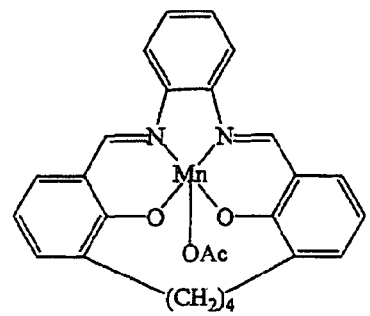
C132:
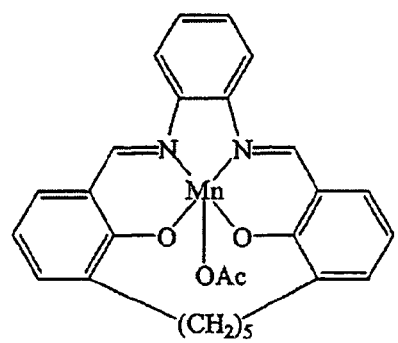
C133:
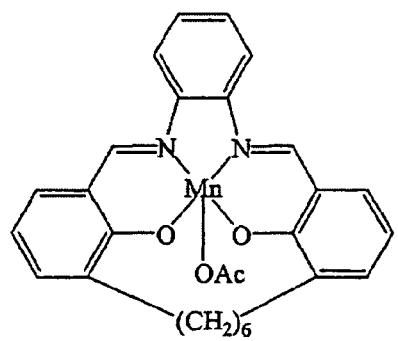
C134:
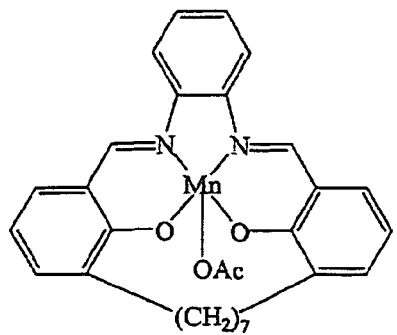
*FIG. 1 CON'T*

C135:
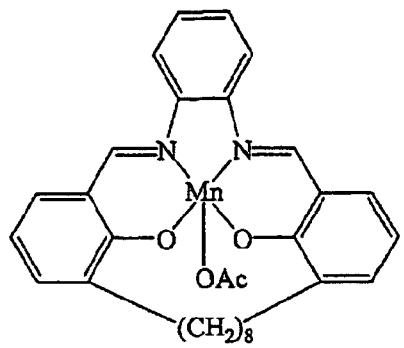
C136:
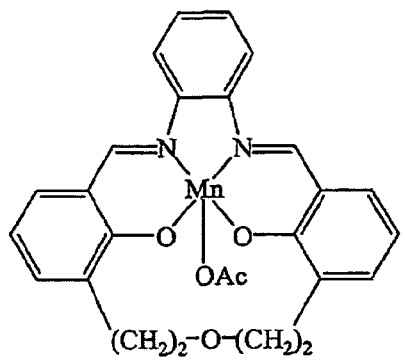
C137:
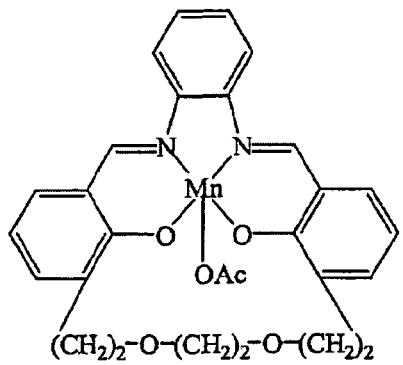
*FIG. 1 CON'T*

C138:
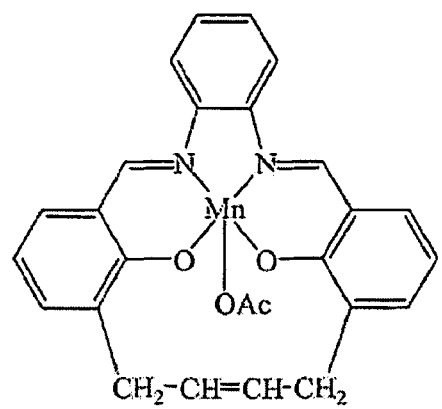
C139:
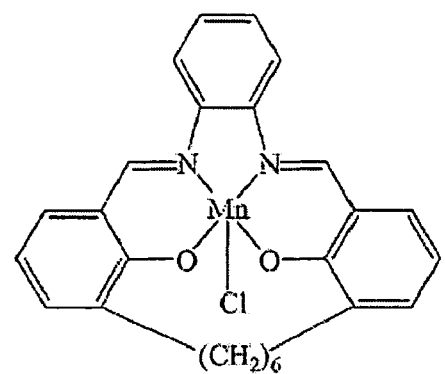
C151:
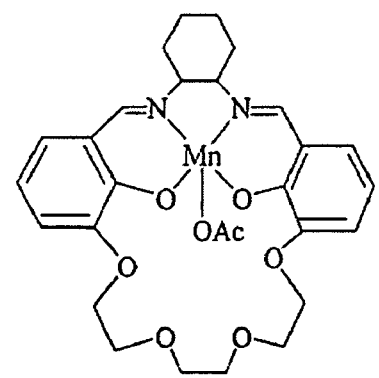
*FIG. 1 CON'T*

C155:
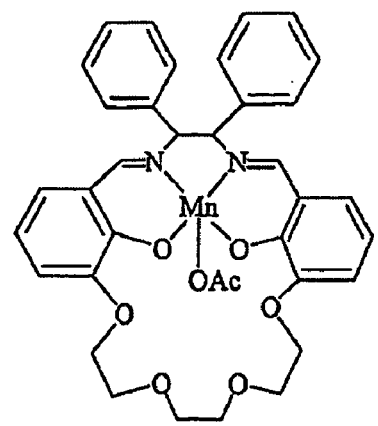
*FIG. 1 CON'T*

CYCLIC SALEN-METAL COMPOUNDS AS SCAVENGERS FOR OXYGEN RADICALS AND USEFUL AS ANTIOXIDANTS IN THE TREATMENT AND PREVENTION OF DISEASES

FIELD OF THE INVENTION

The present invention provides, inter alia, antioxidant compositions, including pharmaceutical compositions, of synthetic catalytic cyclic salen-metal antioxidants and reactive oxygen species scavengers for therapy and prophylaxis of disease and prevention of oxyradical-mediated oxidation; methods of using such cyclic salen-metal antioxidants in the prevention and treatment of pathological conditions; methods of using such cyclic salen-metal antioxidants as preservatives and oxyradical quenching agents; methods of using such cyclic salen-metal antioxidants for targeted protection of tissues and/or cell types during cancer chemotherapy; and methods of using such cyclic salen-metal antioxidants to prevent toxicologic damage to individuals exposed to irritating oxidants or other sources of oxidative damage, particularly oxygen-derived oxidative species, such as the superoxide radical and hydrogen peroxide. In addition, the present invention provides compositions and methods that are useful for preventing oxidative damage in human transplant organs and for inhibiting reoxygenation injury following reperfusion of ischemic tissues. In addition, the present invention provides compositions and methods that are useful for chemoprevention of chemical carcinogenesis and alteration of drug metabolism involving epoxide or free oxygen radical intermediates. The present invention also provides novel cyclic salen-metal compounds (CSMCs) having therapeutically useful catalytic properties, and compositions containing such novel compounds.

BACKGROUND OF THE INVENTION

Molecular oxygen is an essential nutrient for nonfacultative aerobic organisms, including, of course, humans. Oxygen is used in many important ways, namely, as the terminal electronic acceptor in oxidative phosphorylation, in many dioxygenase reactions, including the synthesis of prostaglandins and of vitamin A from carotenoids, in a host of hydroxylase reactions, including the formation and modification of steroid hormones, and in both the activation and the inactivation of xenobiotics, including carcinogens. The extensive P-450 system uses molecular oxygen in a host of important cellular reactions. In a similar vein, nature employs free radicals in a large variety of enzymic reactions.

Excessive concentrations of various forms of reactive oxygen species and of free radicals can have serious adverse effects on living systems, including the peroxidation of membrane lipids, the hydroxylation of nucleic acid bases, and the oxidation of sulfhydryl groups and of other sensitive moieties in proteins. If uncontrolled, mutations and/or cellular death result.

Biological antioxidants include well-defined enzymes, such as superoxide dismutase, catalase, selenium glutathione peroxidase, and phospholipid hydroperoxide glutathione peroxidase. Nonenzymatic biological antioxidants include tocopherols and tocotrienols, carotenoids, quinones, bilirubin, ascorbic acid, uric acid, and metal-binding proteins. Various antioxidants, being both lipid and water soluble, are found in all parts of cells and tissues, although each specific antioxidant often shows a characteristic distribution pattern. The so-called ovothiols, which are mercaptohistidine derivatives, also decompose peroxides nonenzymatically.

Free radicals, particularly free radicals derived from molecular oxygen, are believed to play a fundamental role in a wide variety of biological phenomena. In fact, it has been suggested that much of what is considered critical illness may involve oxygen radical ("oxyradical") pathophysiology (Zimmerman, J. J. (1991) *Chest* 100:189S). Oxyradical injury has been implicated in the pathogenesis of pulmonary oxygen toxicity, adult respiratory distress syndrome (ARDS), bronchopulmonary dysplasia, sepsis syndrome, and a variety of ischemia-reperfusion syndromes, including myocardial infarction, stroke, cardiopulmonary bypass, organ transplantation, necrotizing enterocolitis, acute renal tubular necrosis, and other disease. Oxyradicals can react with proteins, nucleic acids, lipids, and other biological macromolecules producing damage to cells and tissues, particularly in the critically ill patient.

Free radicals are atoms, ions, or molecules that contain an unpaired electron (Pryor, W. A. (1976) *Free Radicals in Biol.* 1:1). Free radicals are usually unstable and exhibit short half-lives. Elemental oxygen is highly electronegative and readily accepts single electron transfers from cytochromes and other reduced cellular components; a portion of the $O_2$ consumed by cells engaged in aerobic respiration is univalently reduced to superoxide radical (i.e., $.O_2^-$) (Cadenas, E. (1989) *Ann. Rev. Biochem.* 58:79). Sequential univalent reduction of $.O_2^-$ produces hydrogen peroxide (ie., $H_2O_2$), a hydroxyl radical (i.e., .OH), and water.

Free radicals can originate from many sources, including aerobic respiration, cytochrome P-450-catalyzed monooxygenation reactions of drugs and xenobiotics (e.g., trichloromethyl radicals, i.e., $CCl_3.$, formed from oxidation of carbon tetrachloride), and ionizing radiation. For example, when tissues are exposed to gamma radiation, most of the energy deposited in the cells is absorbed by water and results in scission of the oxygen-hydrogen covalent bonds in water, leaving a single electron on hydrogen and one on oxygen, thereby creating two radicals, i.e., H. and .OH. The hydroxyl radical, i.e., .OH, is the most reactive radical known in chemistry. It reacts with biomolecules, sets off chain reactions and can interact with the purine or pyrimidine bases of nucleic acids. Indeed, radiation-induced carcinogenesis may be initiated by free radical damage (Breimer, L. H. (1988) *Brit. J Cancer* 57:6). In addition, the "oxidative burst" of activated neutrophils produces abundant superoxide radical, which is believed to be an essential factor in producing the cytotoxic effect of activated neutrophils. Reperfusion of ischemic tissues also produces large concentrations of oxyradicals, typically superoxide (Gutteridge and Halliwell (1990) *Arch. Biochem. Biophys.* 283:223). Moreover, superoxide can be produced physiologically by endothelial cells for reaction with nitric oxide, a physiological regulator, forming peroxynitrite, i.e., $ONOO^-$ which may decay and give rise to hydroxyl radical, .OH (Marletta, M. A. (1989) *Trends Biochem. Sci.* 14:488; Moncada, et al. (1989) *Biochem. Pharmacol* 38:1709; Saran, et al. (1990) *Free Rad. Res. Commun.* 10:221; Beckman, et al. (1990) *Proc. Natl. Acad. Sci. (U.S.A.)* 87:1620). Additional sources of oxyradicals are "leakage" of electrons from disrupted mitochondrial or endoplasmic reticular electron transport chains, prostaglandin synthesis, oxidation of catecholamines, and platelet activation.

Oxygen, though essential for aerobic metabolism, can be converted to poisonous metabolites, such as the superoxide anion and hydrogen peroxide, collectively known as reactive oxygen species (ROS). Increased ROS formation under pathological conditions is believed to cause cellular damage through the action of these highly reactive molecules on proteins, lipids, and DNA. During inflammation, ROS are generated by activated phagocytic leukocytes. As described above; during the neutrophil "respiratory burst," superoxide anion is generated by the membrane-bound NADPH oxidase. ROS are also believed to accumulate when tissues are subjected to ischemia followed by reperfusion.

Many free radical reactions are highly damaging to cellular components, i.e., they crosslink proteins, mutagenize DNA, and peroxidize lipids. Once formed, free radicals can interact to produce other free radicals and non-radical oxidants such as singlet oxygen ($^1O_2$) and peroxides. Degradation of some of the products of free radical reactions can also generate potentially damaging chemical species. For example, malondialdehyde is a reaction product of peroxidized lipids that reacts with virtually any amine-containing molecule. Oxygen free radicals also cause oxidative modification of proteins (Stadtman, E. R. (1992) *Science* 257: 1220).

Aerobic cells generally contain a number of defenses against the deleterious effects of oxyradicals and their reaction products. Superoxide dismutases (SODs) catalyze the reaction:

$$2.O_2^- + 2H^+ \text{---} > O_2 H_2 O_2$$

which removes superoxide and forms hydrogen peroxide. $H_2O_2$ is not a radical, but it is toxic to cells and it is removed by the enzymatic activities of catalase and glutathione peroxidase (GSH-Px). Catalase catalyzes the reaction:

$$2\ H_2O_2 \text{---} > 2\ H_2O + O_2$$

and GSH-Px removes hydrogen peroxide by using it to oxidize reduced glutathione (GSH) into oxidized glutathione (GSSG) according to the following reaction:

$$2\ GSH + H_2O_2 \text{---} > GSSG + 2\ H_2O$$

Other enzymes, such as phospholipid hydroperoxide glutathione peroxidase (PLOOH-GSH-Px), converts reactive phospholipid hydroperoxides, free fatty acid hydroperoxides, and cholesterol hydroperoxides to corresponding harmless fatty acid alcohols. Glutathione S-transferases also participate in detoxifying organic peroxides. In the absence of these enzymes and in presence of transition metals, such as iron or copper, superoxide and hydrogen peroxide can participate in the following reactions which generate the extremely reactive hydroxyl radical, i.e., $.OH^-$:

$$.O_2^- + Fe^{3+} \text{---} > O_2 + Fe^{2+}$$

$$H_2O_2 + Fe^{2+} \text{---} > .OH + OH^- + Fe^{3+}$$

In addition to enzymatic detoxification of free radicals and oxidant species, a variety of low molecular weight antioxidants, such as glutathione, ascorbate, tocopherol, ubiquinone, bilirubin, and uric acid, serve as naturally-occurring physiological antioxidants (Krinsky, N. I. (1992) *Proc. Soc. Exp. Biol. Med.* 200:248–54). Carotenoids are another class of small molecule antioxidants and have been implicated as protective agents against oxidative stress and chronic diseases. Canfield, et al., (1992) *Proc. Soc. Exp. Biol. Med.* 200:260, summarize reported relationships between carotenoids and various chronic diseases, including coronary heart disease, cataract, and cancer. Carotenoids dramatically reduce the incidence of certain premalignant conditions, such as leukoplakia, in some patients.

In order to prevent the damaging effects of free radicals and free radical-associated diseases, great efforts have been made to develop new antioxidants that are efficient at removing dangerous oxyradicals, particularly superoxide and hydrogen peroxide, and that are inexpensive to manufacture, stable and possess advantageous pharmacokinetic properties, such as the ability to cross the blood-brain barrier and penetrate tissues. Most recently, Malfroy-Camine, et aL have achieved this goal with their unexpected discovery that members of a class of compounds that were originally described as epoxidation catalysts, the so-called salen-metal complexes, also exhibit potent superoxide dismutase activity and/or catalase activity and, thus, function effectively as catalysts for free radical removal both in vitro and in vivo (see, U.S. Pat. Nos. 5,403,834, 5,834,509, 5,696,109 and 5,827,880, all of which issued to Malfroy-Camine, the teachings of which are incorporated herein by reference). Prior to this discovery, the salen-transition metal complexes had only been described and used as chiral epoxidation catalysts for various synthetic chemistry applications (see, Fu, et al. (1991) *J. Org. Chem.* 56:6497; Zhang, W. and Jacobsen, E. N. (1991) *J. Org. Chem.* 56:2296; Jacobsen, et al. (1991) *J. Am. Chem. Soc.* 113:6703; Zhang et al. (1990) *J. Am. Chem. Soc.* 112:2801; Lee, N. H. and Jacobsen, E. N. (1991) *Tetrahedron Lett.* 32:6533; Jacobsen, et al. (1991) *J. Am. Chem. Soc.* 113:7063; Lee, et al. (1991) *Tetrahedron Lett.* 32:5055).

Malfroy-Camine, et al. have now found that salen-metal complexes are also useful as potent antioxidants for various biological applications, including their use as pharmaceuticals for the prevention and/or treatment of free radical-associated diseases. Pharmaceutical formulations, dietary supplements, improved cell and organ culture media, improved cryopreservation media, topical ointments, and chemoprotective and radioprotective compositions can now be prepared with an effective amount or concentration of at least one antioxidant salen-metal complex. In addition, Malfroy-Camine, et al. have found that salen-metal complexes can also be used to partially or totally arrest the progression of neurodegenerative diseases. For instance, antioxidant salen-metal complexes can be used for the treatment and prophylaxis of neurodegenerative diseases such as amyotrophic lateral sclerosis (ALS), multiple sclerosis (MS), Parkinson's disease, Alzheimer's disease, etc. Other uses for such salen-metal complexes are disclosed in U.S. Pat. Nos. 5,403,834, 5,834,509, 5,696,109 and 5,827,880.

Although the contributions of Malfroy-Camine, et al. have revolutionized the field of antioxidants that are useful in the prevention and treatment of free radical-associated diseases, it would still be advantageous if salen-metal compounds having increased stability could be developed. The present invention fulfills this and other goals.

SUMMARY OF THE INVENTION

It has now been discovered that the stability of salen-metal compounds or, interchangeably, salen-metal complexes can be increased by cyclizing such compounds at the 3,3'-position. As such, in one aspect, the present invention provides cyclic salen-metal compounds having increased stability. In addition, the present invention provides pharmaceutical compositions comprising such antioxidant cyclic salen-metal compounds, therapeutic uses of such antioxidant cyclic salen-metal compounds, and methods and compositions for using such antioxidant cyclic salen-metal compounds in diagnostic, therapeutic and research applications in, for example, human and veterinary medicine.

In one embodiment, the present invention provides cyclic salen-metal compounds having the following general formula:

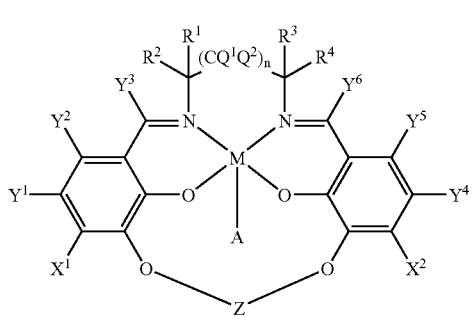

(I)

In another embodiment, the present invention provides cyclic salen-metal compounds having the following general formula:

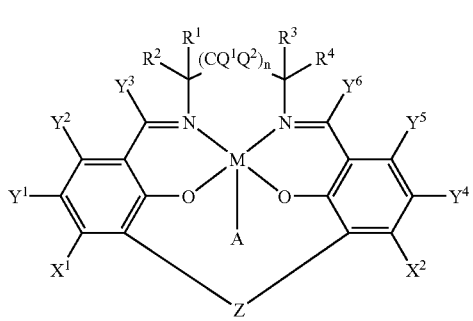

(II)

In Formulae I and II, M is a metal, preferably a transition metal, and A is an anion, preferably a halogen or an organic anion (e.g., acetate). Examples of suitable transition metals include, but are not limited to, Mn, Cr, Fe, Zn, Cu, Ni, Co, Ti, V, Ru and Os. Examples of suitable anions include, but are not limited to, $PF_6^-$, $(Aryl)_4$, $BF_4^-$, $B(Aryl)_4$, halogen, acetate, acetyl, formyl, formate, triflate, tosylate or, alternatively, the anion can be an oxygen atom typically bound via a double bond to the metal, i.e., M. $X^1$ and $X^2$ are independently selected and are functional groups including, but not limited to, hydrogen, halogen, alkyls, substituted alkyls, aryls, substituted aryls, heterocyclics, substituted heterocyclics, heteroaryls, substituted heteroaryls, silyls, aminos, fatty acid esters, alkoxys, aryloxys and acyloxys. $Y^1$, $R^2$, $Y^3$, $Y^4$, $Y^5$ and $Y^6$, in Formulae I and II, are independently selected and are functional groups including, but not limited to, hydrogen, halogen, alkyls, substituted alkyls, aryls, substituted aryls, heterocyclics, substituted heterocyclics, heteroaryls, substituted heteroaryls, silyls, aminos, fatty acid esters, alkoxys, aryloxys and acyloxys. $R^1$, $R^2$, $R^3$ and $R^4$ are independently selected and are functional groups including, but not limited to, hydrogen, halogens, alkyls, substituted alkyls, aryl, substituted aryl, heterocyclics, substituted heterocyclics, heteroaryls, substituted heteroaryls, silyls, aminos, fatty acid esters, alkoxys, aryloxys and acyloxys; with the proviso that one of $R^1$ or $R^2$ may be covalently linked to one of $R^3$ or $R^4$ forming a cyclic structure. Z, in Formulae I and II, is a bridging group. $Q^1$ and $Q^2$, in Formulae I and II, are independently selected and are functional groups including, but not limited to, hydrogen, halogen, alkyls, substituted alkyls, aryls, substituted aryls, heterocyclics, substituted heterocyclics, heteroaryls, substituted heteroaryls, silyls, aminos, fatty acid esters, alkoxys, aryloxys and acyloxys. The index "n" is 0, 1 or 2.

In another aspect, the present invention provides pharmaceutical compositions that have potent antioxidant and/or free radical scavenging properties and function as in vitro and in vivo antioxidants. The pharmaceutical compositions of the present invention comprise an efficacious dosage of at least one species of a cyclic salen-metal complex of Formulae I or II, typically a salen-manganese complex such as a salen-Mn(III) complex. These pharmaceutical compositions possess the activity of dismutating superoxide (i.e., superoxide dismutase activity) and, advantageously, the ability to convert hydrogen peroxide to water and oxygen (i.e., catalase activity). As such, the pharmaceutical compositions of the present invention are effective at reducing pathological damage related to the formation of reactive oxygen species (ROS).

In yet another aspect, the present invention provides methods of using the cyclic salen-metal compounds of the present invention to prevent and/or to treat free radical-associated damage or free radical-associated diseases. More particularly, the present invention provides methods of using cyclic salen-metal compounds to treat or protect a subject undergoing or expected to undergo: (1) an ischemic episode, such as a myocardial infarction, cerebral ischemic event, transplantation operation, open heart surgery, elective angioplasty, coronary artery bypass surgery, brain surgery, renal infarction, traumatic hemorrhage, tourniquet application; (2) antineoplastic or antihelminthic chemotherapy employing a chemotherapeutic agent that generates free radicals; (3) endotoxic shock or sepsis; (4) exposure to ionizing radiation; (5) exposure to exogenous chemical compounds that are free radicals or produce free radicals; (6) thermal or chemical burns or ulcerations; (7) hyperbaric oxygen; (8) apoptosis of a predetermined cell population (e.g. lymphocyte apoptosis); (9) an inflammatory response; or (10) age-related pathological changes or conditions.

More particularly, the present invention provides methods and compositions for the following: (1) preventing ischemic/reoxygenation injury in a patient; (2) preserving organs for transplant in an anoxic, hypoxic, or hyperoxic state prior to transplant; (3) protecting normal tissues from free radical-induced damage consequent to exposure to ionizing radiation (UV light, gamma radiation, etc.) and/or chemotherapy (e.g., with bleomycin); (4) protecting cells and tissues from free radical-induced injury consequent to exposure to xenobiotic compounds that form free radicals, either directly or as a consequence of monooxygenation through the cytochrome P-450 system; (5) enhancing cryopreservation of cells, tissues, organs, and organisms by increasing the viability of recovered specimens; (6) preventing or treating neurological damage and/or neurodegenerative diseases, and (7) prophylactic administration to prevent, for example, carcinogenesis, cellular senescence, cataract formation, formation of malondialdehyde adducts, HIV pathology and macromolecular crosslinking, such as collagen crosslinking.

Other features, objects and advantages of the invention and its preferred embodiments will become apparent from the detailed description which follows.

DETAILED DESCRIPTION OF THE INVENTION AND PREFERRED EMBODIMENTS

I. General Overview

Figure 1:
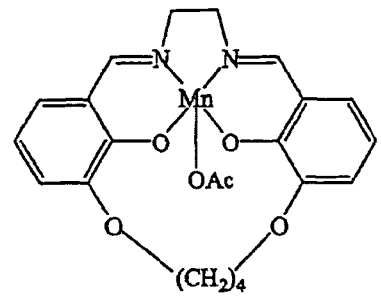
FIG. 1 illustrates preferred cyclic salen-metal compounds of the present invention.
Figure 1:
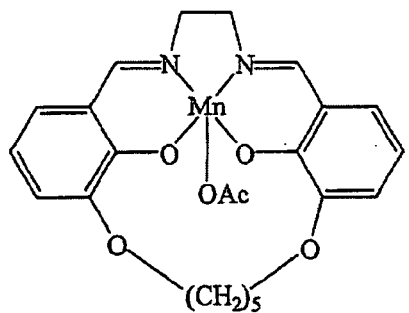
Figure 1:
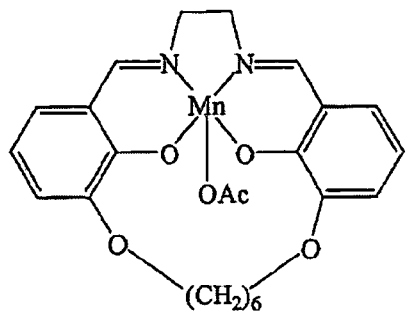
Figure 1:
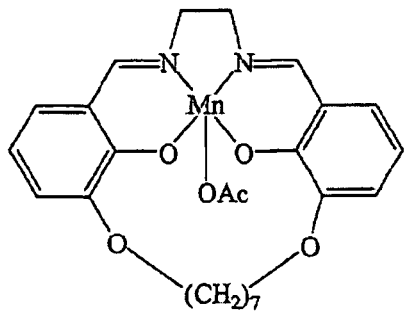

The present invention provides cyclic salen-metal compounds having increased stability. More particularly, the present invention provides salen-metal compounds that are cyclized at the 3,3'-position. Importantly, the cyclic salen-metal compounds of the present invention possess the activity of scavenging superoxide (i.e., superoxide dismutase activity) and, advantageously, the ability to convert hydrogen peroxide to water and oxygen (i.e., catalase activity). As such, the cyclic salen-metal compounds of the present invention have potent antioxidant and/or ROS scavenging properties and function as in vitro and in vivo antioxidants.

Thus, in addition to providing cyclic salen-metal compounds, the present invention provides compositions and methods of using such cyclic salen-metal compounds in the prevention and treatment of pathological conditions; methods of using such cyclic salen-metal compounds as preservatives and oxyradical quenching agents; methods of using such cyclic salen-metal compounds for targeted protection of tissues and/or cell types during cancer chemotherapy; and methods of using such cyclic salen-metal compounds to prevent toxicologic damage to individuals exposed to irritating oxidants or other sources of oxidative damage, particularly oxygen-derived oxidative species, such as the superoxide radical. In addition, the present invention provides compositions and methods for preventing oxidative damage in human transplant organs and for inhibiting reoxygenation injury following reperfusion of ischemic tissues. Moreover, the present invention provides compositions and methods useful for chemoprevention of chemical carcinogenesis and alteration of drug metabolism involving epoxide or free oxygen radical intermediates. Other methods and compositions for using the cyclic salen-metal compounds of the present invention are disclosed herein.

Generally, the nomenclature used hereafter and the laboratory procedures in cell culture, analytical chemistry, organic synthetic chemistry, and pharmaceutical formulation described below are those well known and commonly employed in the art. Standard techniques are used for chemical syntheses, chemical analyses, pharmaceutical formulation and delivery, and treatment of patients.

II. Definitions

Unless defined otherwise, all technical and scientific terms used herein have the same meaning as commonly understood by one of ordinary skill in the art to which this invention belongs. The definitions offered herein are intended to supplement, not supplant the art-accepted definitions.

As used herein, an "antioxidant" is a substance that, when present in a mixture or structure containing an oxidizable substrate biological molecule, significantly delays or prevents oxidation of the substrate biological molecule. Antioxidants can act by scavenging biologically important reactive free radicals or other reactive oxygen species (e.g. $.O_2^-$, $H_2O_2$, $.OH$, $HOCl$, ferryl, peroxyl, peroxynitrite, and alkoxyl), or by preventing their formation, or by catalytically converting the free radical or other reactive oxygen species to a less reactive species. An antioxidant salen-transition metal complex of the invention generally has detectable ROS scavenging activity. A salen-transition metal complex of the invention has antioxidant activity if the complex, when added to a cell culture or assay reaction, produces a detectable decrease in the amount of a free radical, such as superoxide, or a nonradical reactive oxygen species, such as hydrogen peroxide, as compared to a parallel cell culture or assay reaction that is not treated with the complex. The relative amount of free radical species is often determined by detection of a secondary indicator (e.g., an oxidized substrate; peroxidized lipid, reduced NBT, cytochrome c). Suitable concentrations (i.e., efficacious dose) can be determined by various methods, including generating an empirical dose-response curve, predicting potency and efficacy of a congener by using QSAR methods or molecular modeling, and other methods used in the pharmaceutical sciences. Since oxidative damage is generally cumulative, there is no minimum threshold level (or dose) with respect to efficacy, although minimum doses for producing a detectable therapeutic or prophylactic effect for particular disease states can be established. Antioxidant salen metal complexes of the invention may have glutathione peroxidase activity or peroxidase activity in general.

As used herein, a "salen-transition metal complex" refers to a compound having a structure according to Formulae I or II. In Formulae I and II, the axial ligand (A) is typically a halogen or an organic anion (such as acetate, propionate, butyrate or formate). The metal (M) is typically a transition metal (such as Mn, Mg, Co, Fe, Cu, Zn, V, Cr, and Ni; preferably Mn or V and, more preferably, Mn; wherein the typical oxidation state is +3).

As used herein, "free radical-associated disease" refers to a pathological condition of an individual that results at least in part from the production of or exposure to free radicals, particularly oxyradicals, and other reactive oxygen species. It is evident to those of skill in the art that most pathological conditions are multifactorial, in that multiple factors contributing to the disease state are present, and that assigning or identifying the predominant causal factor(s) for any individual pathological condition is frequently extremely difficult. For these reasons, the term "free radical associated disease" encompasses pathological states that are recognized in the art as being conditions wherein damage from free radicals or reactive oxygen species is believed to contribute to the pathology of the disease state, or wherein administration of a free radical inhibitor (e.g., desferrioxamine), scavenger (e.g., tocopherol, glutathione), or catalyst (e.g. SOD, catalase) is shown to produce a detectable benefit by decreasing symptoms, increasing survival, or providing other detectable clinical benefits in treating or preventing the pathological state. For example but not limitation, the disease states discussed herein are considered free radical-associated diseases (e.g., ischemic reperfusion injury, inflammatory diseases, systemic lupus erythematosus, myocardial infarction, stroke, traumatic hemorrhage, brain and spinal cord trauma, Crohn's disease, autoimmune diseases (e.g. rheumatoid arthritis, diabetes), cataract formation, uveitis, emnphysema, gastric ulcers, oxygen toxicity, neoplasia, undesired cell apoptosis, radiation sickness, and other pathological states disclosed herein, such as toxemia and acute lung injury). Such diseases can include "apoptosis-related ROS," which refers to reactive oxygen species (e.g., $O_2^-$, HOOH) which damage critical cellular components (e.g., lipid peroxidation) in cells stimulated to undergo apoptosis, such apoptosis-related ROS may be formed in a cell in response to an apoptotic stimulus and/or produced by non-respiratory electron transport chains (i.e., other than ROS produced by oxidative phosphorylation).

The present invention provides methods for therapy and prophylaxis of free radical-associated disease comprising administering to a patient a therapeutically-effective dose of an antioxidant salen-metal complex pharmaceutical composition. In preferred embodiments, the method is used for preventing, arresting, or treating (1) neurological damage such as Parkinson's disease or Alzheimer's disease, (2) cardiac tissue necrosis resulting from cardiac ischemia, (3) autoimmune neurodegeneration (e.g., encephalomyelitis), (4) acute lung injury such as in sepsis and endotoxemia, (5) neuronal damage resulting from ischemia (e.g., stroke, drowning, brain surgery) or trauma (e.g., concussion or cord shock), and (6) radiation-induced damage.

As used herein the terms "SOD mimetic," "SOD mimic," "superoxide dismutase mimetic," and "superoxide catalyst" refer to compounds that have detectable catalytic activity for the scavenging of superoxide as determined by assay. Generally, an SOD mimetic possesses at least about 0.001 percent of the SOD activity of human Mn-SOD or Zn,Cu-SOD, on a weight basis, as determined by standard assay methods such as for example the SOD assay used herein below.

The term "pharmaceutical agent or drug" as used herein refers to a chemical compound or composition capable of inducing a desired therapeutic effect when properly administered to a patient.

"Substituted," as used herein, generally refers to an alkyl or aryl group that is elaborated with one or more of a wide range of substituents. When "substituted" is used in conjunction with alkyl, the substituent(s) can be pendent from the alkyl group, or the substituent(s) can interrupt the alkyl group, or the substituent(s) can be both pendent from, and interrupt, the alkyl group.

The term "independently selected" is used herein to indicate that the groups so described can be identical or different.

The term "alkyl" is used herein to refer to a branched or unbranched, saturated or unsaturated, hydrocarbon radical having from 1–30 carbons and preferably, from 4–20 carbons and more preferably from 6–18 carbons. When the alkyl group has from 1–6 carbon atoms, it is sometimes referred to as a "lower alkyl." Suitable alkyl radicals include, for example, structures containing one or more methylene, methine and/or methyne groups. Branched structures have a branching motif similar to i-propyl, t-butyl, i-butyl, 2-ethylpropyl, etc. As used herein, the term encompasses "substituted alkyls."

"Substituted alkyl" refers to alkyl as just described including one or more functional groups such as lower alkyl, aryl, acyl, halogen (i.e., alkylhalos, e.g., $CF_3$), hydroxy, amino, alkoxy, alkylamino, acylamino, acyloxy, aryloxy, aryloxyalkyl, mercapto, both saturated and unsaturated cyclic hydrocarbons, heterocycles and the like. These groups may be attached to any carbon of the alkyl moiety.

The term "aryl" or "Ar" is used herein to refer to an aromatic substituent which may be a single aromatic ring or multiple aromatic rings which are fused together, linked covalently, or linked to a common group such as a methylene or ethylene moiety. The common linking group may also be a carbonyl as in benzophenone. The aromatic ring(s) may include phenyl, naphthyl, biphenyl, diphenylmethyl and benzophenone among others. The term "aryl" encompasses "arylalkyl."

The term "alkylarene" is used herein to refer to a subset of "aryl" in which the aryl group is substituted with an alkyl group as defined herein.

"Substituted aryl" refers to aryl as just described including one or more functional groups such as lower alkyl, acyl, halogen, alkylhalos (e.g., $CF_3$), hydroxy, amino, alkoxy, alkylamino, acylamino, acyloxy, mercapto and both saturated and unsaturated cyclic hydrocarbons which are fused to the aromatic ring(s), linked covalently or linked to a common group such as a methylene or ethylene moiety. The linking group may also be a carbonyl such as in cyclohexyl phenyl ketone. The term "substituted aryl" encompasses "substituted arylalkyl."

The term "acyl" is used to describe a ketone substituent, —C(O)R, wherein R is alkyl or substituted alkyl, aryl or substituted aryl as defined herein.

The term "halogen" or "halide" is used herein to refer to fluorine, bromine, chlorine and iodine atoms.

The term "hydroxy" is used herein to refer to the group —OH.

The term "amino" is used to describe primary amines, —NR'R", wherein R' and R" are independently hydrogen, alkyl or substituted alkyl or aryl or substituted aryl as defined herein. The term "quaternary amine" refers to the positively charged group where R', R", and R''' are independently selected and are alkyl or aryl. A preferred amino group is —$NH_2$.

The term "silyl" as used herein refers to organometallic substituents, wherein at least one silicon atom is linked to at least one carbon atom; an example of a silyl substituent is the trimethylsilyl substituent, $(CH_3)_3Si$—. For the purposes of this invention the term "hydrocarbyl" shall refer to an organic radical comprised of carbon chains to which hydrogen and other elements are attached. The term includes alkyl, alkenyl, alkynyl and aryl groups, groups which have a mixture of saturated and unsaturated bonds, carbocyclic rings and includes combinations of such groups. It may refer to straight chain, branched-chain, cyclic structures or combinations thereof.

The term "alkoxy" is used herein to refer to the —OR group, wherein R is a lower alkyl, substituted lower alkyl, aryl, substituted aryl, arylalkyl or substituted arylalkyl wherein the alkyl, aryl, substituted aryl, arylalkyl and substituted arylalkyl groups are as described herein. Suitable alkoxy radicals include, for example, methoxy, ethoxy, phenoxy, substituted phenoxy, benzyloxy, phenethyloxy, t-butoxy, etc.

The term "aryloxy" refers to a group having the structure —O—Ar, where Ar is an aromatic group. A preferred aryloxy group is phenoxy.

The term "alkylamino" denotes secondary and tertiary amines wherein the alkyl groups may be either the same or different and may consist of straight or branched, saturated or unsaturated hydrocarbons.

The term "unsaturated cyclic hydrocarbon" is used to describe a non-aromatic group with at least one double bond, such as cyclopentene, cyclohexene, etc. and substituted analogues thereof.

The term "heteroaryl" as used herein refers to aromatic rings in which one or more carbon atoms of the aromatic ring(s) are substituted by a heteroatom such as nitrogen, oxygen or sulfur. Heteroaryl refers to structures which may be a single aromatic ring, multiple aromatic ring(s), or one or more aromatic rings coupled to one or more non-aromatic ring(s). In structures having multiple rings, the rings can be fused together, linked covalently, or linked to a common group such as a methylene or ethylene moiety. The common linking group may also be a carbonyl as in phenyl pyridyl ketone. As used herein, rings such as thiophene, pyridine, isoxazole, phthalimide, pyrazole, indole, furan, etc. or benzo-fused analogues of these rings are defined by the term "heteroaryl."

"Alkylheteroaryl" defines a subset of "heteroaryl" substituted with an alkyl group, as defined herein.

"Substituted heteroaryl refers to heteroaryl as just described wherein the heteroaryl nucleus is substituted with one or more functional groups such as lower alkyl, acyl, halogen, alkylhalos (e.g. $CF_3$), hydroxy, amino, alkoxy, alkylamino, acylamino, acyloxy, mercapto, etc. Thus, substituted analogues of heteroaromatic rings such as thiophene, pyridine, isoxazole, phthalimide, pyrazole, indole, furan, etc. or benzo-fused analogues of these rings are defined by the term "substituted heteroaryl."

The term "heterocyclic" is used herein to describe a saturated or unsaturated non-aromatic group having a single ring or multiple condensed rings from 1–12 carbon atoms and from 1–4 heteroatoms selected from nitrogen, sulfur or oxygen within the ring. Such heterocycles are, for example, tetrahydrofuran, morpholine, piperidine, pyrrolidine, etc.

The term "substituted heterocyclic" as used herein describes a subset of "heterocyclic" wherein the heterocycle nucleus is substituted with one or more functional groups such as lower alkyl, acyl, halogen, alkylhalos (e.g. $CF_3$), hydroxy, amino, alkoxy, alkylamino, acylamino, acyloxy, mercapto, etc.

The term "alkylheterocyclyl" defines a subset of "heterocyclic" substituted with an alkyl group, as defined herein.

The term "substituted heterocyclicalkyl" defines a subset of "heterocyclicalkyl" wherein the heterocyclic nucleus is substituted with one or more functional groups such as lower alkyl, acyl, halogen, alkylhalos (e.g. $CF_3$), hydroxy, amino, alkoxy, alkylamino, acylamino, acyloxy, mercapto, etc.

The term "fatty acid ester," as used herein, refers to a substituent that is derived from a fatty acid by removal of a hydrogen. When present, the fatty acid esters typically occupy no more than two substituent positions and are usually identical. Examples of fatty acids from which the fatty acid esters can be derived are set forth in Tables I, II, and III, infra.

TABLE I $CH_3—(CH_2)_f—(CH=CH)_g(CH_2)_hCO_2H$

| Carbons | f | g | h | Acid Name |
|---|---|---|---|---|
| 16 | 5 | 1 | 7 | Palmitoleic |
| 18 | 7 | 1 | 7 | Oleic |
| 18 | 10 | 1 | 4 | Petroselenic |
| 18 | 5 | 1 | 9 | Vaccenic |
| 18 | 3 | 3 | 7 | Punicic |
| 18 | 1 | 4 | 7 | Parinaric |
| 20 | 9 | 1 | 7 | Gadoleic |
| 22 | 9 | 1 | 9 | Cetoleic |

TABLE II $CH_3—(CH_2)_n—(CH=CH—CH_2)_m—(CH_2)_p—CO_2H$

| Carbons | n | m | p | Acid Name |
|---|---|---|---|---|
| 18 | 4 | 2 | 6 | Linoleic |
| 18 | 1 | 3 | 6 | Linolenic |
| 20 | 4 | 4 | 2 | Arachidonic |

TABLE III $CH_3—(CH_2)_w—CO_2H$

| Carbons | w | Acid Name |
|---|---|---|
| 12 | 10 | Lauric |
| 14 | 12 | Myristic |
| 16 | 14 | Palmitic |
| 18 | 16 | Stearic |
| 20 | 18 | Eicosanoic |
| 22 | 20 | Docosanoic |

It will be appreciated that the unsaturated fatty acids occur in isomeric forms due to the prescence of the one or more unsaturated positions. The compounds of the present invention are intended to include both the individual double bond isomers as well as mixtures thereof. The fatty acid esters of the present invention can be obtained by known acylation techniques (see, e.g., *March, Advanced Organic Chemistry*, 3rd Ed., John Wiley & Sons, New York (1985), pp. 299, 348–351, and 353–354, incorporated herein by reference.)

Other chemical terms herein are used according to conventional usage in the art, as exemplified by *The McGraw-Hill Dictionary of Chemical Terms* (Parker, S. (ed.), 1985), McGraw-Hill, San Francisco), which is incorporated herein by reference.

III. Cyclic Salen-Metal Compounds

The present invention provides cyclic salen-metal compounds having increased stability. More particularly, the present invention provides salen-metal compounds or, interchangeably, salen-metal complexes that are cyclized at the 3,3 '-position. In a presently preferred embodiment, the present invention provides salen-metal compounds that are cyclized at the 3,3'-position. In one embodiment, the present invention provides cyclic salen-metal compounds having the following general formula:

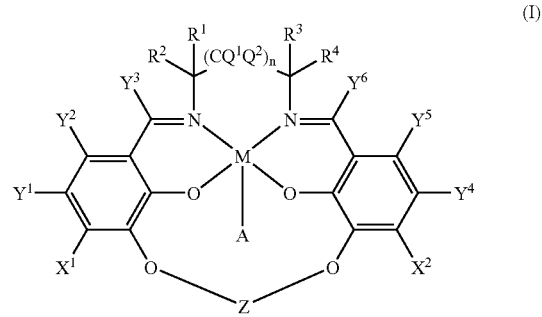

(I)

In another embodiment, the present invention provides cyclic salen-metal compounds having the following general formula:

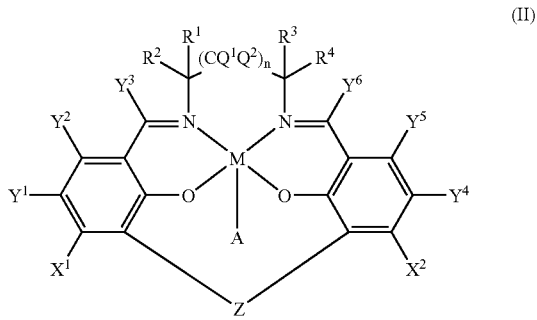

(II)

In Formulae I and II, "M" is a metal. In a presently preferred embodiment, "M" is a transition metal including, but not limited to, Mn, Mg, Co, Fe, Cu, Zn, V, Cr and Ni. In even more preferred embodiments, M is Mn, Cu or Fe. It is noted that when M is a transition metal, the compounds of the present invention are also referred to as "cyclic salen-transition metal compounds or complexes." "A," in Formulae I and II, is an anion. In a preferred embodiment, A is a halogen (chlorine, bromine, fluorine or iodine atoms) or an organic anion (e.g., acetate, propionate, butyrate, formate, and triflate). In presently preferred embodiments, A is chloride or acetate. "$X^1$ and $X^2$" are independently selected and are functional groups including, but not limited to, hydrogen, halogens, alkyls, substituted alkyls, aryls, substituted aryls, heterocyclics, substituted heterocyclics, heteroaryls, substituted heteroaryls, silyls, aminos, fatty acid esters, alkoxys, aryloxys and acyloxys. "$Y^1$, $Y^2$, $Y^3$, $Y^4$, $Y^5$ and $Y^6$," in Formulae I and II, are independently selected and are functional groups including, but not limited to, hydrogen, halogens, alkyls, substituted alkyls, aryls, substituted aryls, heterocyclics, substituted heterocyclics, heteroaryls, substituted heteroaryls, silyls, aminos, fatty acid esters, alkoxys, aryloxys and acyloxys. "$R^1$, $R^2$, $R^3$ and $R^4$" are independently selected and are functional groups including, but not limited to, hydrogen, halogens, alkyls, substituted alkyls, aryl, substituted aryl, heterocyclics, substituted heterocyclics, heteroaryls, substituted heteroaryls, silyls, aminos, fatty acid esters, alkoxys, aryloxys and acyloxys; with the proviso that one of $R^1$ or $R^2$ may be covalently linked to one of $R^3$ or $R^4$ forming a cyclic structure. "Z," in Formulae I and II, is a bridging group, i.e., any group that can be used to form a bridge between the 3 and the 3' positions. "$Q^1$ and $Q^2$" are independently selected and are functional groups including, but not limited to, hydrogen, halogens, alkyls, substituted alkyls, aryls, substituted aryls, heterocyclics, substituted heterocyclics, heteroaryls, substituted heteroaryls, silyls, aminos, fatty acid esters, alkoxys, aryloxys and acyloxys. The index "n" is 0, 1 or 2.

Within the scope of Formulae I and II, certain embodiments of $X^1$ and $X^2$ are preferred. In one such embodiment, $X^1$ and $X^2$ are independently selected and are functional groups including, but not limited to, hydrogen, alkyls, halogens, alkoxys and aminos. In another preferred embodiment, $X^1$ and $X^2$ are both hydrogen. In yet another preferred embodiment, $X^1$ and $X^2$ are both alkoxy. In still another preferred embodiment, $X^1$ and $X^2$ are both alkyls.

Within the scope of Formulae I and II, certain embodiments of $Y^1$, $Y^2$, $Y^3$ and $Y^4$ are preferred. In one such embodiment, $Y^1$, $Y^2$, $Y^3$ and $Y^4$ are independently selected from the group consisting of hydrogen, alkyls, halogens, alkoxys and aminos. In another preferred embodiment, $Y^1$, $Y^2$, $Y^3$, $Y^4$, $Y^5$ and $Y^6$ are all hydrogen. In yet another preferred embodiment, $Y^1$ and $Y^4$ are both halogen, and $Y^2$, $Y^3$, $Y^5$ and $Y^6$ are all hydrogen. In another preferred embodiment, $Y^1$ and $Y^4$ are both amino, and $Y^2$, $Y^3$, $Y^5$ and $Y^6$ are all hydrogen. In still another embodiment, $Y^1$ and $Y^4$ are both alkoxy, and $Y^2$, $Y^3$, $Y^5$ and $Y^6$ are all hydrogen.

Within the scope of Formulae I and II, certain embodiments of "n," $Q^1$, $Q^2$, $R^1$, $R^2$, $R^3$ and $R^4$ are preferred. In one such embodiment, n is 0; and $R^1$, $R^2$, $R^3$ and $R^4$ are all hydrogen. In another preferred embodiment, n is 0; $R^1$ and $R^3$ are both aryloxy; and $R^2$ and $R^4$ are both hydrogen. In yet another preferred embodiment, n is 0; $R^1$ and $R^3$ are both aryl; and $R^2$ and $R^4$ are both hydrogen. In another preferred embodiment, n is 0; $R^1$ and $R^3$ are both aryloxy; and $R^2$ and $R^4$ are both hydrogen. In still another preferred embodiment, n is 0; and one of $R^1$ or $R^2$ is covalently linked to one of $R^3$ or $R^4$ forming a five- or six-membered ring. In a preferred embodiment, one of $R^1$ or $R^2$ is covalently linked to one of $R^3$ or $R^4$ forming a six-membered ring. Examples of preferred six-member rings include, but are not limited to, a cyclohexyl ring, a benzene ring and a pyridine ring. In yet another preferred embodiment, n is 1 and $Q^1$ and $Q^2$ are both hydrogen.

Within the scope of Formulae I and II, certain embodiments of "Z" are preferred. In one such embodiment, the bridging group Z is —$(CH_2)_m$—, wherein "m" is equal to or greater than 1. In this embodiment, "m" is preferably from 2 to 6 and, more preferably, 3. In another preferred embodiment, the bridging group Z is —$(CR^5R^6)_m$—, wherein each $R^5$ and $R^6$ is independently selected and is a functional group including, but not limited to, hydrogen, hydroxy, alkyl, alkoxy, acyl and amino; and "m" is equal to or greater than 1. In this embodiment, "m" is preferably from 2 to 6 and, more preferably, 3. It is noted that the parentheses around $R^5$ and $R^6$ define a monomeric unit. There are "m" monomers in any given bridging group Z. The definitions of $R^5$ and $R^6$ can vary from monomer to monomer for any given value of "m" monomers. In one preferred embodiment, m is equal to or greater than 3 and at least one of the ($CR^5R^6$) monomers is replaced by a heteroatom, such as oxygen, sulfur or nitrogen. Preferably, the heteroatom is oxygen.

Examples of preferred bridging groups, i.e., Z, falling within this embodiment are as follows:

—$CH_2$—$CH_2$—O—$CH_2CH_2$—; and

—$CH_2$—$CH_2$—O—$CH_2$—$CH_2$—O—$CH_2$—$CH_2$—.

In another preferred embodiment, the bridging group Z has the general formula:

—$(CR^7R^8)_m$—$R^9$—$(CR^{10}R^{11})_p$—

In the above formula, each $R^7$, $R^8$, $R^{10}$ and $R^{11}$ is independently selected and is a functional group including, but not limited to, hydroxy, alkyl, alkoxy, acyl and amino. $R^9$, in the above formula, is a functional group including, but not limited to, alkyls, substituted alkyls, cycloalkyls, substituted cycloalkyls, aryls, substituted aryls, heterocyclics, substituted heterocyclics, heteroaryls, substituted heteroaryls and heteroatoms (e.g., oxygen, sulfur and nitrogen). The indexes "m" and "p" are independently selected are equal to 1, 2, 3 or 4. As explained above, the parentheses around $CR^7R^8$ and $CR^{10}R^{11}$ define monomeric units. There are "m" monomers of $CR^7R^8$ and "p" monomers of $CR^{10}R^{11}$ in any given bridging group Z. The definitions of $R^7$, $R^8$, $R^{10}$ and $R^{11}$ can vary from monomer to monomer for any given value of "m" or "p" monomers.

In a preferred embodiment, $R^9$ is aryl (e.g. benzene). In another preferred embodiment, $R^9$ is cycloalkyl (e.g., cyclohexyl). In yet another preferred embodiment, $R^9$ is a saturated or unsaturated alkyl group and, preferably, an unsaturated alkyl group (e.g., alkene). In still another preferred embodiment, $R^9$ is a heteroatom and, preferably, an oxygen atom. Examples of preferred bridging groups, i.e., Z, falling within this embodiment are as follows:

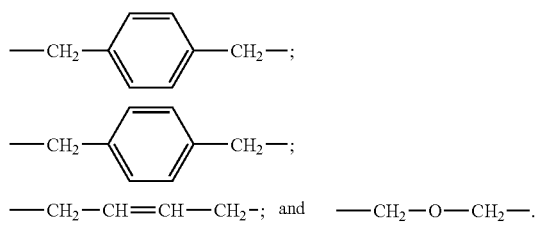

FIG. 1 sets forth cyclic salen-metal compounds in accordance with the present invention that are particularly preferred. The salen-metal compounds in this table and throughout this specification are referred to by compound numbers, which are used for convenience only and are strictly arbitrary for purposes of this invention.

Certain cyclic salen-metal compounds of the present invention possess asymmetric carbon atoms (optical centers) or double bonds; the racemates, diastereomers, geometric isomers and individual isomers are all intended to be encompassed within the scope of the present invention. Optically active (R) and (S), or (D) and (L), isomers can be prepared using chiral synthons or chiral reagents, or resolved using conventional techniques. When the compounds described herein contain olefinic double bonds or other centers of geometric asymmetry, unless specified otherwise, it is intended to include both E and Z geometric isomers. Likewise, all tautomeric forms are intended to be included.

The cyclic salen-metal compounds of the present invention can be synthesized in a variety of ways, using conventional synthetic chemistry techniques. Typically, the compounds of the present invention are prepared according to the reaction scheme set forth in Example I, B. In the first step of this reaction scheme, a 2,3-dihydroxybenzaldehyde is reacted with, for example, an alkyl dihalide to form a 3,3'-alkenedioxy-bis(2-hydroxybenzaldehyde). In the second step, the 3,3'-alkenedioxy-bis(2-hydroxybenzaldehyde) is reacted with a diamine (e.g., 1,2,ethylene diamine, 1,2-phenylene diamine, etc.) and manganese(II) acetate tetrahydrate to form the cyclic salen-metal compound having a 3,3'-bridging group. The use of appropriate organic solvents, temperature and time conditions for running the reactions are within the level of skill in the art.

Other methods can be used to synthesize the cyclic salen-metal compounds of the present invention. For example, methods shown in Schemes 1–4 can be used. As exemplified in Scheme 1, the portion of the ring derived from the diamine is prepared by, for example, forming a Schiff base between an aldehyde i and a diamine. The resulting Schiff base is then reduced by, for example, sodium cyanoborohydride or a similar reducing agent to form ii.

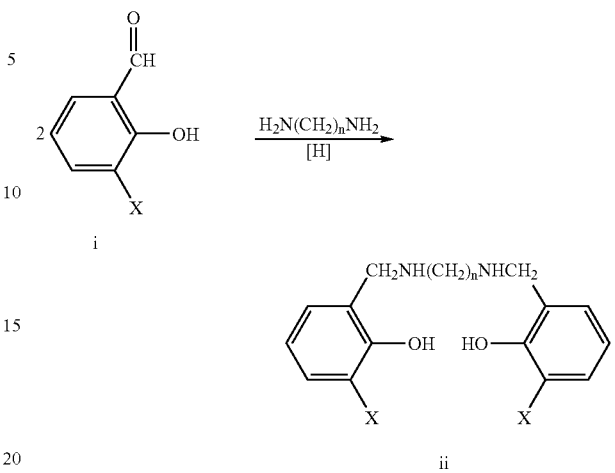

An array of ring closure reactions are useful to form the compounds of the present invention. As exemplified in Scheme 2, diamine-linked phenyl groups bearing leaving groups (e.g., halogen) ii, are reacted with an allyl boronate to form the corresponding cyclic adduct iii. The coupling chemistry of allyl boronates is well-known in the art (see, for example, Miyaura et al., Tetrahedron Lett. 22:127 (1981)). The alkene groups of the resulting macrocycle are subsequently reduced by, for example, hydrogenation to form the compounds of the invention. The hydrogenation of alkenes bearing both electron-donating and electron-withdrawing substituents is well known in the art (see, for example, Rylander, Hydrogenation Methods; Acadernic Press: New York 1985).

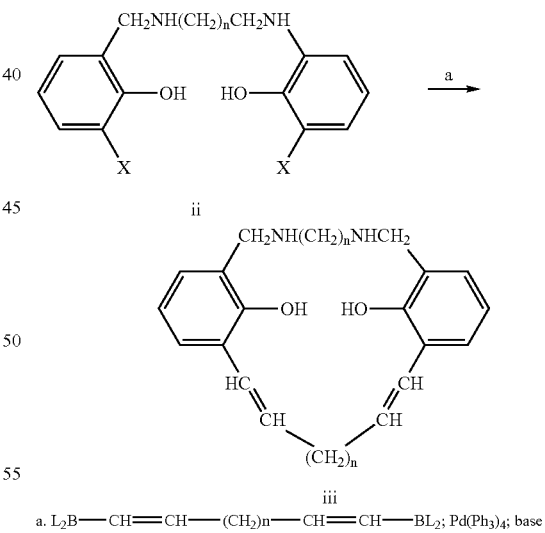

Benzylic moieties bearing leaving groups can also be converted to the macrocycles of the invention by reaction with an allylic boronate. The formation of macrocycles based on benzyhe systems is exemplified in Scheme 3. In Scheme 3, a compound iv in which the benzylic carbon atoms bear a leaving group is coupled to an allyl boronate to close the macrocyclic ring, thereby producing compound v. The alkene groups of the resulting macrocycle are then reduced, as discussed above.

Scheme 3

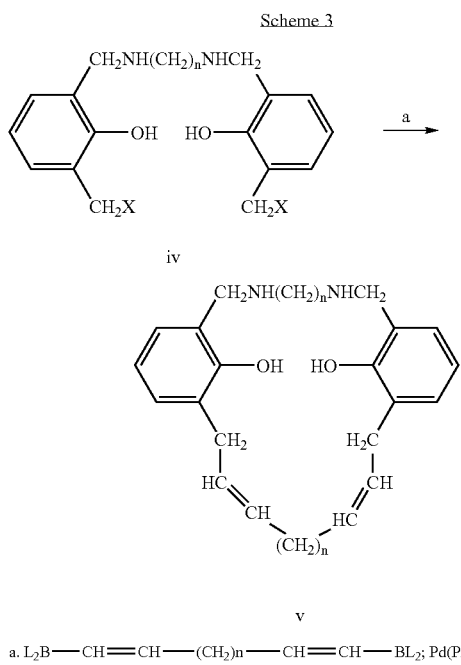

a. L$_2$B—CH≡CH—(CH$_2$)n—CH≡CH—BL$_2$; Pd(Ph$_3$)$_4$; base

The macrocycles of the invention can also be prepared using a method that is based on an olefin metathesis, as exemplified in Scheme 4. Beginning with a compound having two alkene groups, vi, the macrocyclic ring system is closed by olefin metathesis to produce compound vii. Ring closure by olefin metathesis is known in the art (see, for example, Kroll et aL *Chem. Commun.* 839 (1971)). Many olefin methathesis catalysts are Imow in the art and many of these are appropriate catalysts for the reaction set forth in Scheme 4 (see, for example, Grubbs et al., *Acc. Chem. Res.* 28:446–452 (1995)).

Scheme 4

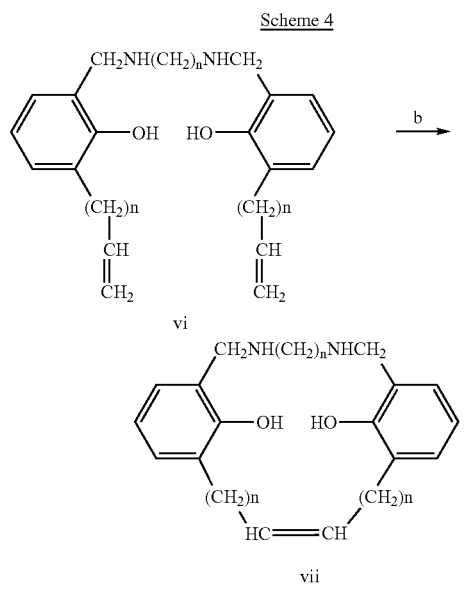

b. olefin metathesis catalyst

Once prepared, the cyclic salen-metal compounds of the present invention can readily be screened for catalytic and biological activities using the assays disclosed herein as well as those disclosed in U.S. Pat. Nos. 5,403,834, 5,834,509, 5,696,109 and 5,827,880 and PCT Patent Application No. PCT/US96/10267. For instance, the SOD activity of the prepared cyclic salen-metal compounds can be determined using standard assay methods for SOD activity known in the art and exemplified infra. Cyclic salen-metal compounds having at least 0.001 percent of human SOD activity on a weight basis in aqueous solution are antioxidant salen-metal compounds. In preferred embodiments, the antioxidant cyclic salen-metal compounds have at least about 0.01 percent of SOD activity per unit weight and, more preferably, at least about 0.1 percent of SOD activity per unit weight. In addition, as set forth in the Examples section, infra, the cyclic salen-metal compounds of the present invention can readily be screened for other catalytic activities (e.g., catalase activity, peroxidase activity, etc.) and other biological activities using standard assays known to and used by those of skill in the art.

IV. Methods of Using Cylic Salen-Metal Compounds

In another embodiment, the present provides methods of using the cyclic salen-metal compounds of Formulae I and II to prevent and/or to treat free radical-associated damage or free radical-associated diseases. In one preferred embodiment, pharmaceutical compositions comprising at least one antioxidant cyclic salen-transition metal complex of the invention is used to treat or protect a patient undergoing or expected to undergo: (1) an ischemic episode, such as a myocardial infarction, cerebral ischemic event, transplantation operation, open heart surgery, elective angioplasty, coronary artery bypass surgery, brain surgery, renal infarction, traumatic hemorrhage, tourniquet application; (2) antineoplastic or antihelninthic chemotherapy employing a chemotherapeutic agent that generates free radicals; (3) endotoxic shock or sepsis; (4) exposure to ionizing radiation; (5) exposure to exogenous chemical compounds that are free radicals or produce free radicals, (6) thermal or chemical burns or ulcerations; (7) hyperbaric oxygen; or (8) apoptosis of a predetermined cell population (e.g., lymphocyte apoptosis).

In another aspect of the invention, a therapeutic or prophylactic dosage of a cyclic salen-metal complex of Formulae I or II is administered either alone or in combination with, for example, one of the following: (1) one or more antioxidant enzymes, such as a Mn-SOD, a Cu,Zn-SOD, or catalase; and/or (2) one or more free radical scavengers, such as tocopherol, ascorbate, glutathione, DMTU, N-acetylcysteine, or N-2-mercaptopropionylglycine; and/or (3) one or more oxyradical inhibitors, such as desferrioxamine or allopurinol; and/or (4) one or more biological modifier agents, such as calpain inhibitors. As will be readily apparent to those of skill in the art, the actual formulation used will depend, for example, on the specific pathological condition sought to be treated or prevented, the route and form of administration, and the age, sex, and condition of the patient. Such compositions can be administered for various indications including, but not limited to, the following: (1) for preventing ischemic/reoxygenation injury in a patient; (2) for preserving organs for transplant in an anoxic, hypoxic, or hyperoxic state prior to transplant; (3) for protecting normal tissues from free radical-induced damage consequent to exposure to ionizing radiation and/or chemotherapy, as with bleomycin; (4) for protecting cells and tissues from free radical-induced injury consequent to exposure to xenobiotic compounds that form free radicals, either directly or as a consequence of monooxygenation through the cytochrome P-450 system; (5) for enhancing cryopreservation of cells, tissues, organs, and organisms by increasing the viability of recovered specimens; and (6) for prophylactic administration to prevent, for example, carcinogenesis, cellular senescence, cataract formation, formation of malondialdehyde adducts, HIV pathology and macromolecular crosslinking, such as collagen crosslinking.

In still another aspect, the present invention provides methods for treating and preventing pathological conditions by applying or administering compositions of cyclic salen-metal complexes in a therapeutic or prophylactic dosage. More particularly, the invention provides methods for preventing or reducing ischemic/reperfusion damage to critical tissues, such as the myocardium and central nervous system. The invention also provides methods for preventing or reducing cellular damage resulting from exposure to various chemical compounds that produce potentially damaging free radical species and ionizing radiation, such as UV light or ionizing radiation. Such methods typically comprise administering to a subject a therapeutically or prophylactically efficacious dosage of at least one species of a cyclic salen-transition metal complex of Formulae I or II, preferably a cyclic salen-manganese complex having detectable SOD activity and, preferably, detectable catalase activity. As described herein, such antioxidant cyclic salen-transition metal complexes can be administered by a variety of routes, including parenterally, topically, and orally.

In other aspects, the invention provides methods for enhancing the recovery of skin of a warm-blooded animal from wounds, such as surgical incisions, burns, inflammation (e.g., psoriasis, atopic dermatitis, etc.), ulcers (e.g., gastric ulcers, diabetic ulcers, etc.) or minor irritation due to oxidative damage, etc. Such methods typically comprise administering to the skin wound or irritation a therapeutically or, in some cases, a prophylactically effective amount of a cyclic salen-metal complex of Formulae I or II.

In another aspect of the invention, antioxidant cyclic salen-metal complexes of Formulae I and II are employed to modulate the expression of naturally-occurring genes or other polynucleotide sequences under the transcriptional control of an oxidative stress response element (e.g., an antioxidant responsive element, ARE), such as an antioxidant response element of a glutathione 5-transferase gene or a NAD(P)H:quinone reductase gene. The antioxidant salen-metal complexes may be used to modulate the transcription of ARE-regulated polynucleotide sequences in cell cultures (e.g., ES cells) and in intact animals, particularly in transgenic animals, wherein a transgene comprises one or more AREs as transcriptional regulatory sequences.

The invention also provides methods for preventing food spoilage and oxidation by applying to foodstuffs an effective amount of at least one antioxidant cyclic salen-metal complex. The invention also provides compositions for preventing food spoilage comprising an effective amount of at least one species of antioxidant cyclic salen-metal complex of Formulae I or II, optionally in combination with at least one additional food preservative agent (e.g., butylated hydroxytoluene, butylated hydroxyanisole, sulfates, sodium nitrite, sodium nitrate). For instance, an antioxidant cyclic salen-metal complex is incorporated into a foodstuff subject to rancidification (e.g., oxidation) to reduce the rate of oxidative decomposition of the foodstuff when exposed to molecular oxygen.

In another aspect, the invention relates to antioxidant compositions and methods of using such compositions to inhibit formation of undesired hydrocarbon polymers generated via free radical-mediated polymerization mechanisms, especially oxyradical-mediated polymerization and/or oxyradical-mediated rancidification or gum formation. The antioxidant cyclic salen-metal complexes of the invention can be applied to a variety of hydrocarbons to reduce undesired oxidation and/or polymerization, or to quench a polymerization reaction at a desired state of polymer formation (e.g., at a desired molecular weight or average chain length). Examples of such saturated and unsaturated hydrocarbons include, but are not limited to, petroleum distillates and petrochemicals, turpentine, paint, synthetic and natural rubber, vegetable oils and waxes, animal fats, polymerizable resins, polyolefin, and the like.

The invention also relates to methods of using the cyclic salen-metal compounds in hydrocarbon compositions to reduce and/or control the formation of undesired polymers that contaminate such hydrocarbon compositions, including hydrocarbons present in aqueous systems, two-phase aqueous:organic systems, and organic solvent systems. This invention relates to a method and composition for controlling the formation of polymers in such systems that comprises an antioxidant composition having an antioxidant cyclic salen-metal compound, optionally in combination with an antioxidant or stabilizer other than a salen-metal compound (e.g., BHT, BHA, catechol, tocopherol, hydroquinone, etc.). The amount of the individual ingredients of the antioxidant composition will vary depending upon the severity of the undesirable polymer formation encountered due to free radical polymerization as well as the activity of the salen-metal compound utilized.

As explained above, the present invention also provides cyclic salen-metal compounds that have peroxidase activity and, therefore, that are capable of serving as effective peroxidase replacements. Such compounds are useful as drugs for the prevention of many pathological conditions including, but not limited to, neoplasia, apoptosis of somatic cells, skin aging, cataracts, and the like; and as antioxidants for scavenging $H_2O_2$ and other peroxides. In addition, the cyclic salen-metal compounds of the present invention can be used in diagnostic assays. For instance, the salen-metal compounds of the present invention can be used in numerous diagnostic assays in place of the traditionally used scavenging antioxidants, such as horseradish peroxidase. It will be readily apparent to those of skill in the art that the salen-metal compounds of the present invention can be used in diagnostic assays in a manner similar to horseradish peroxidase and the other scavenging antioxidants.

The present invention also provides a method of reducing $H_2O_2$ and/or other peroxides that comprises contacting $H_2O_2$ and/or other peroxides with a suitable amount of any of the compounds of the invention effective to reduce $H_2O_2$ and/or other peroxides. Additionally, the invention provides a method of treating a peroxide-induced condition in a subject that comprises administering to the subject an amount of any of the compounds of the invention effective to reduce peroxide in a subject, thereby treating the peroxide-induced condition. Further, the invention provides a pharmaceutical composition that comprises an amount of any of the compounds of the invention effective to reduce peroxide in a subject with a peroxide-induced condition and a pharmaceutically acceptable carrier. Further, the invention provides a method of treating a peroxide-induced condition in a subject, e.g., a human subject, that comprises administering, e.g., by topical, oral, intravenous, intraperitoneal, intramuscular, intradermal, or subcutaneous administration, to the subject an amount of an antioxidant salen-metal compound effective to reduce peroxide in the subject, thereby treating the peroxide-induced condition. The peroxide-induced condition may involve cataracts, inflammation of a tissue, ischemia, an allergic reaction, or pathology caused by oxidative stress. Where the peroxide-induced condition involves cataracts, administration is effected by, but is not limited to, topical contact to the surface of an eye.

Other methods of using the cyclic salen-metal compounds of Formulae I and II will be readily apparent to those of skill in the art from a reading of this disclosure and are intended to be within the scope of the present invention.

V. Pharmaceutical Formulations

In another aspect of the present invention, pharmaceutical compositions are provided, the pharmaceutical compositions comprising a therapeutically or prophylactically effective amount of at least one cyclic salen-metal compound, preferably a cyclic salen-transition metal compound and a pharmaceutically acceptable carrier, excipient or adjuvant. The composition used in carrying out the methods of the present invention can be in a variety of forms. Such forms include, for example, solid, semi-solid and liquid dosage forms, such as tablets, pills, powders, liquid solutions or suspensions, liposome preparations, inhalable, injectable and infusible solutions. The preferred form depends on the intended mode of administration and therapeutic or prophylactic application. Typically, a sterile solution of a cyclic salen-metal complex in an aqueous solvent (e.g. saline) will be administered intravenously. The compositions also preferably include conventional pharmaceutically acceptable carriers and adjuvants which are known to those of skill in the art. See, e.g., *Remington's Pharmaceutical Sciences*, Mack Publishing Co.: Easton, Pa., 17th Ed. (1985). Generally, administration will be by oral or parenteral (including subcutaneous, intramuscular, intravenous, and intradermal) routes, or by topical application or infusion into a body cavity, or as a bathing solution for tissues during surgery.

It should, of course, be understood that the methods and compositions of the present invention can be used in combination with other antioxidant agents that have SOD activity, catalase activity, peroxidase activity, or with other agents that are free radical scavengers or inhibitors of free radical formation. While it is possible to administer the active ingredient, i.e., the cyclic salen-metal complex, of this invention alone, it is preferably delivered as part of a pharmaceutical formulation. The pharmaceutically acceptable formulations of the present invention comprise at least one cyclic salen-metal compound in a therapeutically or pharmaceutically effective dose together with one or more pharmaceutically or therapeutically acceptable carriers and, optionally, other therapeutic ingredients. The various considerations that go into formulating a therapeutic or prophylactic agent are described, e.g., in Gilman, et aL (eds) (1990) *Goodman and Gilman's: The Pharmacological Bases of Therapeutics*, 8th Ed., Pergamon Press; and *Remington's*, supra, each of which is hereby incorporated herein by reference. Methods for administration are discussed therein, e.g., for oral, intravenous, intraperitoneal, or intramuscular administration, and others modes of administration.

As used herein, the term "pharmaceutically acceptable carrier" encompasses any of the standard pharmaceutical carriers such as sterile solutions, tablets, coated tablets, and capsules. Typically such carriers contain excipients such as starch, milk, sugar, certain types of clay, gelatin, stearic acids or salts thereof, magnesium or calcium stearate, talc, vegetable fats or oils, gums, glycols, or other known excipients. Such carriers may also include flavor and color additives or other ingredients. Examples of pharmaceutically acceptable carriers include, but are not limited to, the following: water, saline, buffers, inert, nontoxic solids (e.g., mannitol, talc), and other compounds described, e.g., in the Merck Index (Merck & Co., Rahway, N.J., incorporated herein by reference).

Compositions comprising such carriers are formulated by well known conventional methods. Depending on the intended mode of administration and the intended use, the compositions may be in the form of solid, semi-solid, or liquid dosage forms, such, for example, as powders, granules, crystals, liquids, suspensions, liposomes, pastes, creams, salves, etc., and may be in unit-dosage forms suitable for administration of relatively precise dosages. For semi-solid compositions, as would be appropriate for pastes and creams intended for topical administration, the cyclic salen-metal complexes can be provided separately or may be compounded with conventional nontoxic carriers such as, for example, aloe vera gel, squalane, glycerol stearate, polyethylene glycol, cetyl alcohol, stearic acid, and propylene glycol, among others. Such compositions may contain about 0.005–100% active ingredient, more preferably about 0.5–25%. The concentration of the salen-metal complexes in these formulations can vary widely, and will be selected primarily by intended use, viscosities, etc., in accordance with the particular mode of administration selected. The composition or formulation to be administered will, in any event, contain a quantity of the cyclic salen-metal complexes sufficient to achieve the desired therapeutic or prophylactic effect in the subject being treated. Typical compositions include lotions containing water and/or alcohols and emollients, such as hydrocarbon oils and waxes, silicone oils, vegetable, animal or marine fats or oils, glyceride derivatives, fatty acids or fatty acid esters or alcohols or alcohol ethers, lecithin, lanolin and derivatives, polyhydric alcohols or esters, wax esters, sterols, phospholipids and the like, and generally also emulsifiers (nonionic, cationic or anionic), although some of the emollients inherently possess emulsifying properties. These same general ingredients can be formulated into a cream rather than a lotion, or into gels, or into solid sticks by utilization of different proportions of the ingredients and/or by inclusion of thickening agents such as gums or other forms of hydrophilic colloids. Such compositions are referred to herein as dermatologically acceptable carriers.

In one embodiment, the pharmaceutical compositions of the present invention will be administered by parenteral or oral administration for prophylactic and/or therapeutic treatment. The pharmaceutical compositions can be administered in a variety of unit dosage forms depending upon the method of administration. For example, unit dosage forms suitable for oral administration include powder, tablets, pills, capsules, and dragees.

For oral administration, a pharmaceutically acceptable non-toxic composition is formed by the incorporation of any of the normally employed excipients, such as, for example pharmaceutical grades of mannitol, lactose, starch, magnesium stearate, talcum, celluloses, glucose, sucrose, magnesium, carbonate, and the like. Such compositions take the form of solutions, suspensions, tablets, capsules, powders, sustained release formulations and the like. Such compositions may contain 0.01–95% active ingredient, preferably 1–70%.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

A more recently devised approach for parenteral administration employs the implantation of a slow-release or sustained-release system, such that a constant level of dosage is maintained. See, e.g., U.S. Pat. No. 3,710,795, which is incorporated herein by reference. Antioxidant cyclic salen-metal complexes may be administered by transdermal patch (e.g., iontophoretic transfer) for local or systemic application.

The compositions for parenteral administration will commonly comprise a solution of an antioxidant cyclic salen-metal complex or a cocktail thereof dissolved in an acceptable carrier, preferably an aqueous carrier or organic solvent (e.g., ethanol, solvated PEG, etc.). Since many of the cyclic salen-metal complexes of the invention are lipophilic, it is preferable to include in the carrier a hydrophobic base (e.g., polyethylene glycol, Tween 20, etc.). A variety of aqueous carriers can be used, e.g., water, buffered water, 0.9% saline, 0.3% glycine and the like. These solutions are sterile and generally free of particulate matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example sodium acetate; sodium chloride, potassium chloride, calcium chloride, sodium lactate, etc. The concentration of the antioxidant cyclic salen-metal complex(es) in these formulations can vary widely, i.e., from less than about 1 nM, usually at least about 1 µM to as much as 100 mM and will be selected primarily based on fluid volumes, viscosities, etc., in accordance with the particular mode of administration selected. Most usually, the antioxidant cyclic salen-metal complex is present at a concentration of 0.1 mM to 10 mM. For example, a typical formulation for intravenous injection comprises a sterile solution of an antioxidant cyclic salen-metal complex at a concentration of 1 to 5 mM in physiological saline or Ringer's solution. The generally hydrophobic nature of some of the preferred antioxidant cyclic salen-metal complexes indicates that a hydrophobic vehicle can be used, or that an aqueous vehicle comprising a detergent or other lipophilic agent (e.g., Tween, NP-40, PEG) can be used. Alternatively, the antioxidant cyclic salen-metal complexes can be administered as a suspension in an aqueous carrier or as an emulsion.

As such, a typical pharmaceutical composition for intramuscular injection can be made so that it contains 1 ml sterile water, and about 0.1–100 mg of an antioxidant cyclic salen-metal complex(es). A typical composition for intravenous infusion can be made up to contain 250 ml of sterile saline or Ringer's solution, and about 10–1000 mg of an antioxidant cyclic salen-metal complex(es). Lipophilic agents may be included in formulations of lipophilic cyclic salen-metal complexes. Actual methods for preparing parenterally administratable compositions are well-known or apparent to those skilled in the art and are described in more detail in, for example, *Remington's Pharmaceutical Science*, 15th Ed., Mack Publishing Company, Easton, Pa. (1980), which is incorporated herein by reference. A typical pharmaceutical composition for topical application can be made with suitable dermal ointments, creams, lotions, ophthalmic ointments and solutions, respiratory aerosols, and other excipients. Excipients should be chemically compatible with the antioxidant cyclic salen-metal complex(es), which is the primary active ingredient(s) of the preparation, and generally should not increase decomposition, denaturation, or aggregation of active ingredient(s). Frequently, excipients will have lipophilic components such as oils and lipid emulsions.

As described herein, the pharmaceutical compositions of the present invention can also be administered intravenously. Thus, this invention provides compositions for intravenous administration which comprise a solution of the compound dissolved or suspended in an acceptable carrier, preferably an aqueous carrier. A variety of aqueous carriers can be used, e.g., water, buffered water, 0.9% saline, and the like. Often, the antioxidant cyclic salen-metal complex(es) can be dissolved in an organic solvent and either applied directly or diluted into an aqueous solvent. Typically, antioxidant cyclic salen-metal complexes that are relatively lipophilic are dissolved in an organic solvent and, if desired, subsequently diluted into a more polar solvent, such as water. These compositions will sometimes be sterilized by conventional, well known sterilization techniques, or can preferably be sterile filtered. The resulting aqueous solutions can be packaged for use as is, or lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, and the like.

For solid compositions, conventional nontoxic solid carriers can be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 0.001–95% of active ingredient, preferably about 20%.

Kits can also be supplied for use with the subject antioxidant cyclic salen-metal complex(es) for use in the protection against or therapy for free radical- associated damage or free radical-associated diseases. Thus, the subject composition of the present invention can be provided, usually in a lyophilized form or aqueous solution in a container, either alone or in conjunction with additional antioxidant salen-metal complex(es), cyclic or otherwise, of the desired type. The antioxidant cyclic salen-metal complex(es) are included in the kits with buffers, such as Tris, phosphate, carbonate, etc., stabilizers, biocides, inert proteins, e.g., serum albumin, or the like, and a set of instructions for use. Generally, these materials will be present in less than about 5% wt. based on the amount of antioxidant cyclic salen-metal complex(es), and will usually be present in total amount of at least about 0.001% based again on the concentration. Frequently, it will be desirable to include an inert extender or excipient to dilute the active ingredients, where the excipient may be present in from about 1 to 99.999% wt. of the total composition.

Moreover, the cyclic salen-metal complexes of the present invention can be incorporated into a hypothermic cardioplegia solution at a concentration of at least about 1 mM according to Amano, et al. (1982) *Jpn. J: Surg.* 12:87, incorporated herein by reference.

As explained herein, the dosage of SOD-mimetic cyclic salen-metal complex(es) will vary with each particular application. Typically, the composition is administered either systemically or topically. Systemic administration includes per os and parenteral routes, whereas topical administration includes in situ applications. The in situ means includes, for example, administering an SOD-mimetic cyclic salen-metal complex by endoscopic bolus wash and/or paravenous injection, or in the case of lower GI treatments, by enema. As explained above, parenteral routes include, for example, subcutaneous, intradermal, intramuscular, and intravenous routes. The amount of SOD-mimetic cyclic salen-metal complex(es) will range from about 0.02 to 5,000 mg or more, typically from about 1 to 1000 mg, depending on the administration interval and route, which can range from a single oral dose, parenteral dose and/or topical lose to multiple oral doses, parenteral doses, and/or topical loses over a few days or greater than 5 weeks. Again, the dosage may also vary with the severity of the disease.

As will be readily apparent to those of skill in the art, the antioxidant salen-metal complex(es) of this invention can be lyophilized for storage and reconstituted in a suitable carrier prior to use. In addition, it will be appreciated by those of skill in the art that although not anticipated, lyophilization and reconstitution can lead to varying degrees of antioxidant activity loss and, thus, use levels may have to be adjusted to compensate for such loss.

Moreover, it will be readily apparent to those of skill in the art that the cyclic salen-metal compounds of the present invention can be used either alone or in combination with other known antioxidants and therapeutic agents. For instance, in preferred embodiments, at least one species of an antioxidant cyclic salen-metal complex is administered in combination with one or more other active ingredient including, but not limited to, N-2-mercaptopropionylglycine, N-acetylcysteine, glutathione, dimethyl thiourea, desferrioxamine, mannitol, a-tocopherol, ascorbate, allopurinol, 21-aminosteroids, calpain inhibitors, glutamate receptor antagonists, tissue plasminogen activator, streptokinase, urokinase, nonsteroidal anti-inflammatory agent, cortisone, and carotenoids. Antioxidant cyclic salen-metal complexes can also be administered in conjunction with polypeptides having SOD and/or catalase activity, particularly in view of the ability of the cyclic salen-metal complexes of the present invention to cross the blood-brain barrier (unlike most SOD polypeptides), thereby complementing systemic SOD administration.

Since oxidative damage occurs proportionately to the abundance of free radicals and reactive oxygen species, it is expected that administration of antioxidant cyclic salen-transition metal complexes at even low levels will confer a protective effect against oxidative damage. As such, it is expected that there is no threshold level below which antioxidant cyclic salen-metal complexes are ineffective.

As explained herein, a therapeutically or pharmaceutically effective amount of an antioxidant salen-transition metal complex is administered to a patient to treat or prevent a free radical-associated disease. The required dosage will depend upon the nature of the free radical-associated disease, the severity and course of the disease, previous therapy, the patient's health status and response to the antioxidant salen-transition metal complex, and the judgment of the treating physician. In general, for treatment of free radical-associated diseases, a suitable effective dose of the antioxidant cyclic salen-metal complex will be in the range of 0.001 to 1000 milligram (mg) per kilogram (kg) of body weight of recipient per day, preferably in the range of 0.1 to 100 mg per kg of body weight per day. Single or multiple administrations of the compositions can be carried out with dose levels and dosing pattern being selected by the treating physician. In any event, the pharmaceutical formulations should provide a quantity of the antioxidant salen-transition metal complex(es) of this invention sufficient to effectively treat the patient. In a preferred embodiment, the desired dosage is presented in one, two, three, four or more subdoses administered at appropriate intervals throughout the day. These subdoses can be administered as unit dosage forms, for example, containing 0.01 to 10,000 mg, preferably 1 to 1000 mg of active ingredient per unit dosage form.

Again, compositions containing the antioxidant cyclic salen-metal complex(es) of the present invention, or cocktails thereof, can be administered for prophylactic and/or therapeutic treatments. In therapeutic application, the compositions are administered to a patient already affected by the particular free radical-associated disease, in an amount sufficient to cure or at least partially arrest the condition and its complications. An amount adequate to accomplish this is defined as a "therapeutically effective dose or amount" or "efficacious dose or amount." Amounts effective for this use will depend upon the severity of the condition, the general state of the patient, and the route of administration, but generally range from about 1 mg to about 10 g of antioxidant cyclic salen-metal complex(es) per dose, with dosages of from 10 mg to 2000 mg per patient being more commonly used. For instance, when treating acute myocardial ischemia/reoxygenation episodes, about 10 to 1000 mg of an antioxidant cyclic salen-metal complex can be administered systemically by intravenous infusion or, alternatively, about 1 mg to 500 mg of an antioxidant cyclic salen-metal complex(es) can be administered by intrapericardial injection to provide elevated local concentrations of SOD activity in the myocardium.

In prophylactic applications, compositions containing the antioxidant salen-transition metal complex(es), or cocktails thereof, can be administered to a patient that is not already in a disease state in order to enhance the patient's resistance or to retard the progression of disease. Such an amount is defined as a "prophylactically effective dose or amount." In this use, the precise amounts again depend upon the patient's state of health and general level of immunity, but generally range from 1 mg to 10 g per dose, especially 10 to 1000 mg per patient. A typical formulation of an antioxidant cyclic salen-metal complex will contain between about 2.5 and 250 mg of the cyclic salen-metal complex in a unit dosage form.

Once a detectable improvement in the patient's conditions has occurred, a maintenance dose is administered if necessary. Subsequently, the dosage, the frequency of administration or both can be reduced, as a function of the symptoms, to a level at which the improved condition is maintained. When the symptoms have been alleviated to the desired level, treatment can cease. Patients can, however, require intermittent treatment on a long-term basis upon any recurrence of the disease symptoms or as a prophylactic measure to prevent disease symptom recurrence.

I. Other Uses and Compositions for the Cyclic Salen-Metal Compounds

A. Use of Cyclic Salen-Metal Compounds to Protect Blood, Tissues and Organs

In another aspect, the antioxidant cyclic salen-metal complex(es) of the present invention can be added to extravasated blood for transfusion to inhibit oxyradical damage to the blood cells and components during storage. In addition, such antioxidant cyclic salen-metal complexes can also be used to reduce oxyradical damage to blood cells in vivo or ex vivo.

Antioxidant cyclic salen-metal complex(es) can also be added to perfusion, rinse or storage solutions for organs and tissues, such as for organ transplantation or for surgical rinses. For example, excised organs are often placed in a preservation solution prior to transplant into a recipient. Inclusion of at least one species of an antioxidant cyclic salen-metal complex in a preservation solution, usually at a concentration of about 0.01 mM to about 10 mM, is desirable for reducing damage due to ischemia during storage and reperfusion injury following reimplantation in the recipient. Various solutions described in the art are suitable for the inclusion of a salen-metal complex including, but not limited to, those described in U.S. Pat. No. 5,145,771; Beyersdorf (1990) *Chem. Abst.* 113:84849w; U.S. Pat. Nos. 4,879,283; 4,873,230; and 4,798,824, all of which are incorporated herein by reference.

Typically, the antioxidant cyclic salen-metal complex is present in the rinse or storage solution at a concentration of about 1 µM to about 1 mM and, more preferably, at a concentration of about 10 to 100 µM. For example, but not to limit the invention, a suitable rinse solution comprises Ringer's solution (102 mM NaCl, 4 mM KCl, 3 mM $CaCl_2$, 28 mM sodium lactate, pH 7.0) or Ringer's solution with 0.1 mM adenosine, and one of the antioxidant cyclic salen-metal complexes of the present invention at a final concentration of 50 µM. The rinse solution can further comprise additional antioxidants (e.g., glutathione, allopurinol, etc.). Preservation, perfusion or rinse solutions containing an antioxidant cyclic salen-metal complex can be used to provide enhanced storage or irrigation of organs (e.g., kidney, liver, pancreas, lung, fetal neural tissue, heart, vascular grafts, bone, ligament, tendon, skin, cornea, etc.), which is believed to enhance the viability of the tissue and increase resistance to oxidative damage (e.g., as a consequence of ischemia/reperfusion).

Alternatively, the capacity of the antioxidant cyclic salen-metal complexes to catalyze the decomposition of reactive oxygen species can advantageously be used to inhibit or slow damage to biological tissues and cells. For example, benzoyl peroxide is a widely used treatment for acne lesions. However, excessive or inappropriate application of benzoyl peroxide (e.g., accidental application to the eyes) may be treated by local (or if desired, systemic) administration of an antioxidant cyclic salen-metal complex of the present invention. Similarly, oxyradical-induced damage to connective tissues (e.g., collagen) attendant to exposure to UV light, cigarette smoking, and senescence may be reduced by administration of an antioxidant salen-metal complex approximately concomitant with the exposure to UV light, cigarette smoking, or other oxyradical-generating process (e.g., cellular senescence).

B. Use of Cyclic Salen-Metal Compounds For Cheinoprotection and Radioprotection

Antioxidant cyclic salen-metal complexes, typically antioxidant cyclic salen-transition metal complexes, can be used to protect cells and tissues from free radical-producing agents, such as ionizing radiation (e.g., ultraviolet radiation, gamma (γ)-radiation, etc.) and chemotherapeutic agents (e.g., bleomycin). Preferably, a protective dosage comprising at least about 1 µg of a cyclic salen-metal complex/kg body weight is administered by one or more of several routes (e.g., oral, intravenous, intraperitoneal, intragastric lavage, enema, portal vein infusion, topical, or inhalation of mist). The antioxidant cyclic salen-metal complexes are preferably pre-administered to the patient prior to the commencement of the chemotherapy and/or radiotherapy, usually within about 24 hours of commencement, and preferably within about 3–6 hours of commencement of the chemotherapy and/or radiotherapy. Antioxidant cyclic salen-metal complexes can be continually administered to the patient during the course of therapy and/or after therapy (e.g., immediately after the therapy treatment).

In a preferred embodiment, the administration is by injection of liposomes or immunoliposomes for targeted delivery of the antioxidant cyclic salen-metal complexes to protect normal cells, for example, against free radical toxicity associated with chemotherapy or radiotherapy of, for example, a neoplasm. For instance, a solution of an antioxidant salen-metal complex can be encapsulated in micelles to form immunoliposomes (see, U.S. Pat. Nos. 5,043,164, 4,957,735, 4,925,661; Connor and Huang (1985) *J Cell BioL* 101:582; Lasic, D. D. (1992) *Nature* 355:279; *Novel Drug Delivery* (eds. Prescott L. F. and Nimmo W. S.: Wiley, New York, 1989); and Reddy, et al. (1992) *J. Immunol.* 148:1585; all of which are incorporated herein by reference). The immunoliposomes containing the antioxidant cyclic salen-metal compound can comprise a targeting moiety (e.g., a monoclonal antibody) that targets the immunoliposomes to either non-neoplastic or neoplastic cells that are otherwise sensitive to radiotherapy or chemotherapy. For example, immunoliposomes having a monoclonal antibody that binds specifically to a hematopoietic stem cell antigen not present on the cancer cells of the individual may be used to target antioxidant cyclic salen-metal complexes to hematopoietic stem cells, thereby protecting the stem cells against radiotherapy or chemotherapy used to treat the cancer. Such a strategy is preferably employed when the chemotherapeutic agent forms free radicals in vivo (e.g., bleomycin).

Antioxidant cyclic salen-metal complexes can also be administered to individuals to prevent radiation injury or chemical injury by free radical generating agents. For instance, military personnel and persons working in the nuclear, nuclear medicine and/or chemical industries can be administered cyclic salen-metal complexes prophylactically. Antioxidant salen-metal complexes can also be used as chemoprotective agents to prevent chemical carcinogenesis; particularly by carcinogens which form reactive epoxide intermediates (e.g., benzo-[a]-pyrene, benzanthracene) and by carcinogens or promoting agents that form free radicals directly or indirectly (e.g., phenobarbital, TPA, benzoyl peroxide, peroxisome proliferators: ciprofibrate, clofibrate, etc.). Persons exposed to such chemical carcinogens can be pretreated with an antioxidant cyclic salen-metal complex to reduce the incidence or risk of developing neoplasia.

Antioxidant salen-metal complexes can also be formulated into a lipophilic base (or, if desired, an aqueous carrier) for topical application in cosmetics or sunburn-prevention creams and lotions. A typical cosmetic or sunburn-prevention cream or lotion will comprise about between 1 µg to 50 mg of an antioxidant cyclic salen-metal complex per gram of cosmetic or sunburn-prevention cream or lotion. When used to prevent the deleterious effects of ultraviolet (UV) light exposure to skin, the cyclic salen-metal complex is topically applied to the skin prior to UV light exposure, in conjunction with UV light exposure or after UV light exposure. In a preferred embodiment, the cyclic salen-metal complex is topically applied to the skin prior to, during and after UV light exposure.

Antioxidant cyclic salen-metal complexes can also be administered to deep-sea divers or individuals exposed to hyperbaric environments were oxygen toxicity presents a health risk. Administration of an efficacious dose of an antioxidant cyclic salen-metal complex to an individual may permit the breathing of hyperbaric and/or oxygen-enriched gases with a reduced risk of oxygen toxicity. It is also believed that administration of an efficacious dosage of an antioxidant cyclic salen-metal complex can reduced toxicity and biological damage associated with exposure to ozone. Prophylactic administration of an antioxidant cyclic salen-metal complex to humans who are or will be exposed to ozone is expected to confer an enhanced resistance to ozone toxicity, such as the ozone-induced lung damage noted in geographical areas with high ozone levels (e.g., Los Angeles).

C. Use of Cyclic Salen-Metal Compounds in Cosmetic Formulations

As described above, the antioxidant cyclic salen-metal complexes of the present invention can be formulated into a cosmetic base for topical application and/or for reducing oxidation of the cosmetic by molecular oxygen and oxyradicals. In a presently preferred embodiment, an antioxidant cyclic salen-metal complex is added to a topical cosmetic formulation to prevent the deleterious effects of ultraviolet light exposure to skin. In another preferred embodiment, an antioxidant cyclic salen-metal complex is added to a topical cosmetic formulation to prevent or retard the aging of skin.

D. Use of Cyclic Salen-Metal Compounds in Anti-Inflammatory Compositions

In another aspect, the present invention provides compositions useful for treating inflammation. In a preferred embodiment, a cyclic salen-metal compound is formulated in a pharmaceutically acceptable form with a carrier, excipient or adjuvant. In another preferred embodiment, a cyclic salen-metal compound is formulated in a cosmetic base or dental liniment (e.g., periodontal disease) for topical application for local prevention of inflammation and/or tissue damage consequent to inflammation (e.g., psoriasis, atopic dermatitis, etc.). As will be readily apparent to those of skill in the art, the cyclic salen-metal complexes of the present invention can be used on their own to treat inflammation or, alternatively, they can be used in combination with other known anti-inflammatory agents. A variety of steroidal and nonsteroidal anti-inflammatory agents can be combined with an antioxidant cyclic salen-metal compound of the present invention and used to treat inflammation.

Examples of suitable steroidal anti-inflammatory agents include, but are not limited to, corticosteroids, such as hydrocortisone, hydroxyltriamcinolone, alpha-methyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluocinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fluradrenolone acetonide, medrysone, amcinafel, amcinafide, betamethasone and the balance of its esters, chloroprednisone, chloroprednisone acetate, clocortolone, clescinolone, dichlorisone, difluprednate, flucloronide, flunisolide, fluoromethalone, fluperolone, fluprecinisolone, hydrocortisone valerate, hydrocortisone cyclopentylpropionate, hydrocortamate, pammethasone, prednisolone, prednisone, triamcinolone, and mixtures thereof may be used. In a preferred embodiment, the cyclic salen-metal complex of the present invention is used in combination with hydrocortisone.

Examples of suitable nonsteroidal anti-inflammatory agents include, but are not limited to, piroxicam, isoxicam, tenoxicam, sudoxicam, CP-14,304, aspirin, disalcid, benorylate, trilisate, safapryn, solprin, diflunisal, fendosal, diclofenac, fenclofenac, indomethacin, sulindac, tolmetin, isoxepac, furofenac, tiopinac, zidometacin, acemetacin, fentiazac, zomepirac, clidanac, oxepinac, felbinac, mefenamic, meclofenamic, flufenamic, niflumic, tolfenamic acids, ibuprofen, naproxen, benoxaprofen, flurbiprofen, ketoprofen, fenoprofen, fenbufen, indoprofen, pirprofen, carprofen, oxaprozin, pranoprofen, miroprofen, tioxaprofen, suprofen, alminoprofen, tiaprofenic, phenylbutazone, oxyphenbutazone, feprazone, azapropazone, trimethazone and the like. Mixtures of these nonsteroidal anti-inflammatory agents can also be employed, as well as the pharmaceutically-acceptable salts and esters of these agents. Of the nonsteroidal anti-inflammatory agents, ibuprofen, ketoprophen, naproxen, flufenamic acid, mefenamic acid, meclofenamic acid, piroxicam and felbinac are preferred and ibuprofen, naproxen, and flufenamic acid are most preferred. In addition, etofenamate, a flufenamic acid derivative, is particularly useful for topical application.

Finally, so-called "natural" anti-inflammatory agents are useful in the present invention. For example, candelilla wax, alpha bisabolol, aloe vera, Manjistha (extracted from plants in the genus Rubia, particularly Rubia Cordifolia), and Guggul (extracted from plants in the genus Commiphora, particularly Commiphora Mukul) can also be used.

The pharmaceutical/cosmetic compositions of the present invention formulated, for example, as solutions typically include a pharmaceutically- or cosmetically-acceptable organic solvent. The terms "pharmaceutically-acceptable organic solvent" and "cosmetically-acceptable organic solvent" refer to an organic solvent which, in addition to being capable of having dispersed or dissolved therein a cyclic salen-metal compound of the present invention and, optionally, another anti-inflammatory agent, also possesses acceptable safety (e.g., irritation and sensitization characteristics) as well as good aesthetic properties (e.g., does not feel greasy or tacly). The most typical example of such a solvent is isopropanol. Examples of other suitable organic solvents include, but are not limited to, propylene glycol, polyethylene glycol (200–600), polypropylene glycol (425–2025), glycerol, 1,2,4-butanetriol, sorbitol esters, 1,2,6-hexanetriol, ethanol, butanediol, water and mixtures thereof Typically, these solutions contain from about 0.0001% to about 20%, preferably from about 0.01% to about 1%, of an antioxidant cyclic salen-metal complex and, optionally, from about 0.01% to about 5%, preferably from about 0.5% to about 2% of an anti-inflammatory agent, and from about 80% to about 99%, preferably from about 90% to about 98%, of an acceptable organic solvent.

As used herein, "emollients" refer to materials used for the prevention or relief of dryness, as well as for the protection of the skin. A wide variety of suitable emollients are known to those of skill in the art and may be used herein (see, Sagarin, Cosmetics, *Science and Technology*, 2nd Edition, Vol. 1, pp. 32–43 (1972),which is incorporated herein by reference and which contains numerous examples of suitable materials). Examples of classes of useful emollients include, but are not limited to, the following: hydrocarbon oils and waxes; silicone oils; triglyceride esters; acetoglyceride esters; ethoxylated glycerides; alkyl esters of fatty acids having 10 to 20 carbon atoms; alkenyl esters of fatty acids having 10 to 20 carbon atoms; fatty acids having 10 to 20 carbon atoms; fatty alcohols having 10 to 20 carbon atoms; fatty alcohol ethers; ether-esters such as fatty acid esters of ethoxylated fatty alcohols; lanolin and derivatives; polyhydric alcohols and polyether derivatives; polyhydric alcohol esters; wax esters such as beeswax, spermaceti, myristyl myristate, stearyl stearate; beeswax derivatives; vegetable waxes including carnauba and candelilla waxes; phospholipids, such as lecithin and derivatives; sterols; and amides. A more detailed listing setting forth exemplar members of each of these classes of useful emollients can be found in U.S. Pat. Nos. 5,403,834, 5,834,509, 5,696,109 and 5,827,880.

Particularly useful emollients are those that impart skin conditioning properties and include, for example, glycerol, hexanetriol, butanetriol, lactic acid and its salts, urea, pyrrolidone carboxylic acid and its salts, amino acids, guanidine, diglycerol and triglycerol. In addition, other preferred skin conditioning agents are the propoxylated glycerol derivatives.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES

I. Example I

This example illustrates the preparation of salen-metal compounds and, in particular, cyclic salen-metal compounds having a bridging group at the 3,3'-position.

A. General Method for the Preparation of Salen-Metal Compounds:

Step I: Preparation of 2-hydroxy-3-alkyloxybenzaldehyde:

To a suspension of NaH (2.3 equivalents) in dry DMSO (10 ml/g) under Argon is added a solution of 2,3-dihydroxybenzaldehyde (1 equivalent) in dry DMSO (4 ml/g), over a period of 1 h, under vigorous stirring. The temperature was kept below 25° C. After stirring for 1 h, 1 equivalent of RX, i.e., the alkyl halide (chloride, bromide or iodide), was added in 1 portion. This mixture was stirred for 24 h. This mixture was then quenched with water. The resulting solution was extracted twice with ethyl acetate. These organic extracts, which contain small amounts of the unreacted alkyl halide, were discarded. The aqueous layer was acidified with 6M HCl to a pH of about 1 and extracted thrice with ethyl acetate. These combined organic extracts were washed with water, dried over $Na_2SO_4$ (anhyd.), and concentrated to give a crude product. The crude product was column purified on Silica gel using a gradient solvent system of ethyl acetate and hexane. Yield: 60%. The product was confirmed by NMR analysis.

Step II: Preparation of Manganese Salen Complexes:

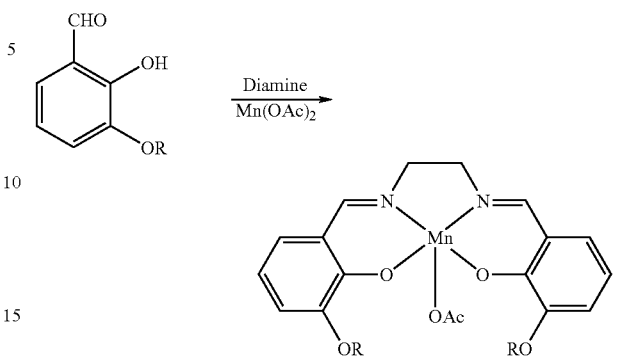

2-hydroxy-3-alkyloxybenzaldehyde (1 equivalent) was dissolved in absolute ethanol (15 ml/g). 1,2,ethylene diamine (1 equivalent) and manganese(II) acetate tetrahydrate (1 equivalent) were added to the solution, and the mixture was stirred for 24 h. Compressed air (or oxygen) was blown over the reaction mixture for 4 h, to complete the oxidation process. The reaction mixture was then concentrated on a rotary evaporator, and the residue obtained was triturated with acetone, filtered and dried. Yield 80%. The crude product was crystallized from methanol-ether. The product was confirmed by elemental analysis.

B. General Method for the Preparation of Cyclized Salen-Metal Compounds:

Step I: Preparation of 3,3'-alkenedioxy-bis(2-hydroxybenzaldehyde)

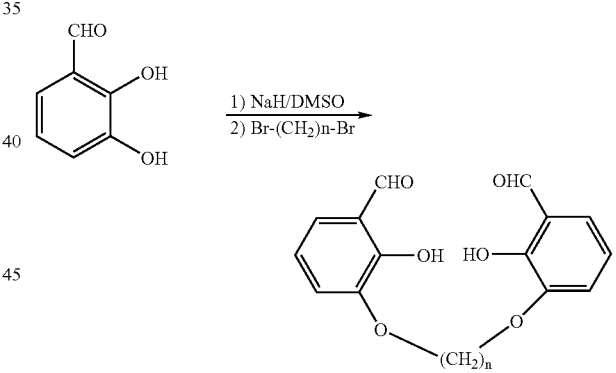

To a suspension of NaH (2.3 equivalents) in dry DMSO (10 ml/g) under Argon is added a solution of 2,3-dihydroxybenzaldehyde (1 equivalent) in dry DMSO (4 ml/g), over a period of 1 h, under vigorous stirring. The temperature was kept below 25° C. After stirring for 1 h, 0.47 equivalent of the alkyl dihalide (chloride, bromide or iodide) was added in 1 portion. This mixture was stirred for 24 h. This mixture was then quenched with water. The resulting solution was extracted twice with ethyl acetate. These organic extracts, which contain small amounts of the unreacted alkyl dihalide, were discarded. The aqueous layer was acidified with 6M HCl to a pH of about 1 and extracted thrice with ethyl acetate. These combined organic extracts washed with water, dried over $Na_2SO_4$ (anhyd.), and concentrated to give a crude product. The crude product was column purified on Silica gel using a gradient solvent system of ethyl acetate and hexane. Yield: 60%. The product was confirmed by NMR analysis.

Step II: Preparation of Cyclized Salen-Metal Compounds:

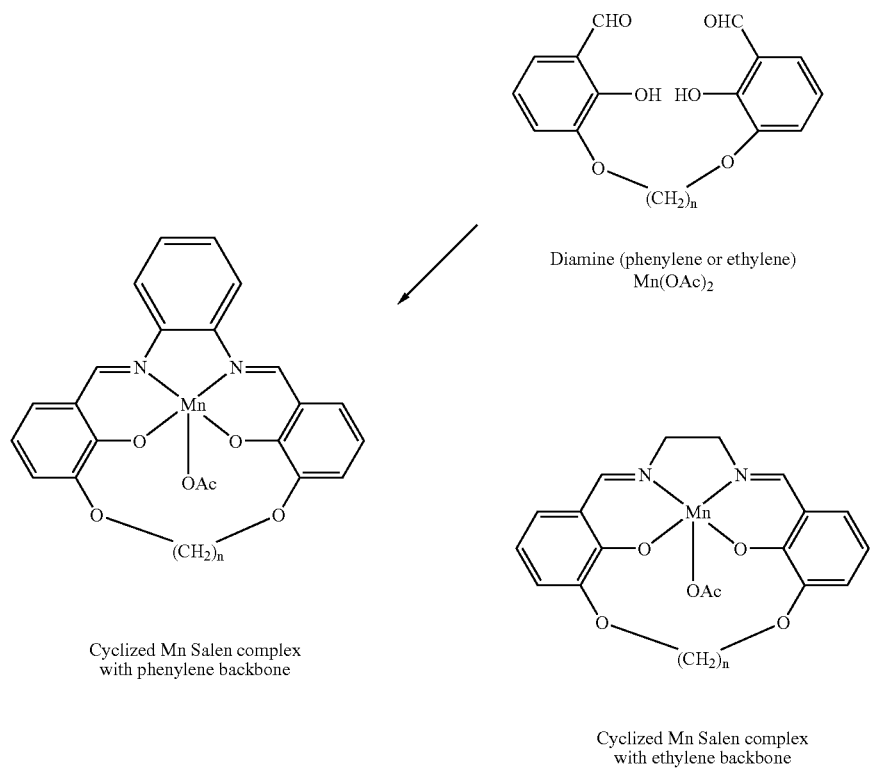

Cyclized Mn Salen complex with phenylene backbone

Cyclized Mn Salen complex with ethylene backbone

The bis-aldehyde (I equivalent) was dissolved in absolute ethanol (1333 ml/g). The diamine (1 equivalent of 1,2-phenylene diamine or 1,2,ethylene diamine) and manganese (II) acetate tetrahydrate are added to the solution, and the mixture was stirred for 24 h. Compressed air (or oxygen) was blown over the reaction mixture for 4 h, to complete the oxidation process. The reaction mixture was then concentrated on a rotary evaporator, and the residue obtained was triturated with acetone, filtered and dried. Yield 80%. The crude product was crystallized from methanol-ether. The product was confirmed by elemental analysis and GPC analysis.

C. General Method For the Preparation of C155:

This example ilustrates a method that can be used to prepare CI55, which is also referred to herein as FC-06-155.

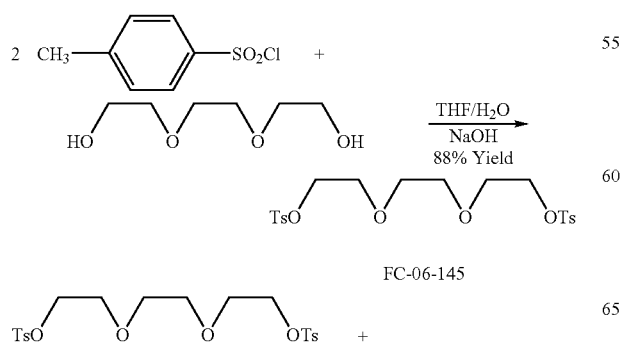

FC-06-145

-continued

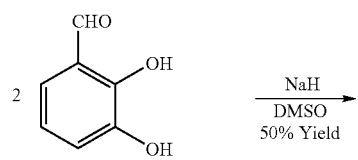

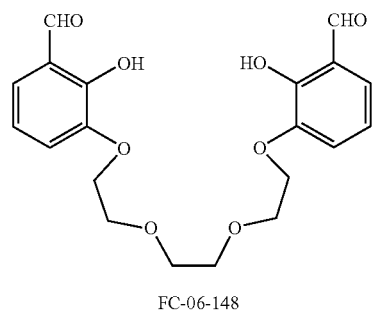

FC-06-148

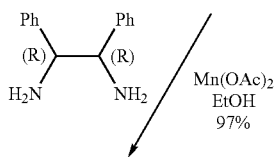

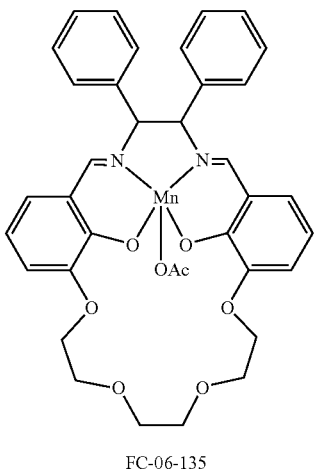

FC-06-135

1. Experimental Procedure

General. All starting materials were obtained from Aldrich and used as received. All moisture-sensitive reactions were performed under an atmosphere of dry nitrogen. Dry DMSO was obtained by distillation over 4A activated molecular sieves and keep on 4A activated molecular sieves.

2. II-1-Triethylene glycol ditoluene-4-sulfonate (FC-06-145)

The procedure followed was from Cornforth, J. W., et al., *Tetrahedron*, 1973, 29,1659–1667, the teachings of which are incorporated herein by reference.

A solution of toluene-4-sulfonyl chloride (84g) in THF (150 mL) was added in small portions with shaking, to a solution of tri-(ethylene glycol) (30 g) and NaOH (21 g) in water (100 mL). The mixture was shaken for 2 h and left overnight. The product was extracted with toluene, the toluene extract washed with water, diluted $Na_2CO_3$ aq and water, dried ($CaCl_2$) and evaporate to dryness. The residue was crystallized from toluene/ether; The precipitate was filtrated, washed several times with ether, leading to a white powder (80.96 g, 88% Yield).

$^1$H NMR ($CDCl_3$) δ7.80 (d, J=8.4 Hz, 4H, HAr), 7.35 (d, J=8.4 Hz, 4H, HAr), 4.15 (m, 4H, $TsOCH_2CH_2O$), 3.66 (m, 4H, $TsOCH_2CH_2O$), 3.41 (S, 4H, $OCH_2CH_2O$), 2.46 (s, 6H, $CH_3$); mass spectrometry, (EI, 70 eV) m/z=286 (M-TsOH, 0.69%); Anal. Calcd for $C_{20}H_{26}O_8S_2$: C, 52.39; H, 5.72. Found: C, 52.67 ; H, 5.31.

3. II-2-3,3'-(3,6-Dioxaoctane-1,8-diyldioxy)bis(2-hydroxybenzaldehyde) (FC-06-148)

The procedure followed was from Van Staveren, C. J., *J. Am. Chem. Soc.*, 1998, 110,4994–5008, the teachings of which are incorporated herein by reference.

To a suspension of NaH (60% in oil) under $N_2$ (6.48 g, 0.16) in 35 mL of dry DMSO, a solution of 2,3-dihydroxybensaldehyde (10.18 g, 0.073 mol) in 40 mL of dry DMSO was added over a period of 2 h, under a vigorous stirring. The temperature was kept below 25° C. After stirring for 1 h (FC-06-145) (16.73 g, 0.036 mol) was added in one portion. This mixture was stirred 24 h at room temperature. Subsequently 300 mL of water was added, and this aqueous layer was acidified with 6M HCl to pH=1 and extracted with $CHCl_3$ (1L). Combined organic layers were dried over $MgSO_4$. After removal of solvent a crude product was obtained which was purified by column chromatography ($CH_2Cl_2$, iPrOH 2.5%). Layers containing the product with Rf=0.35 were combined and solvent were removed. MeOH was added to the sticky orange oil until the compound precipitated. The precipitate was filtered off and dried under vacuum, leading to a slightly yellow solid (6.3 g, 44% Yield).

$^1$HNMR ($CDCl_3$) δ10.88 (s, 2H, OH), 9.95 (s, 2H, CHO), 7.19 (m, 4H, HAr), 6.92 (m, 2H, HAr), 4.22 (t, J=5.1 Hz, 4H, $ArOCH_2CH_2O$), 3.90 (t, J=5.1 Hz, 4H, $ArOCH_2CH_2O$), 3.78 (s, 4H, $OCH2CH_2O$); mass spectrometry, (EI, 70 eV) m/z=390 (M+, 18.47%); IR (Nujol) 1637 (C═O) $cm^{-1}$; Anal. Calcd for $C_{20}H_{22}O_8$: C, 61.53; N, 5.68. Found: C, 60.67; H, 5.40.

4. II-3-EUK-500 (FC-06-155 or C155)

(FC-06-148) was previously crushed in order to obtain a very fine powder. (FC-06-148) (0.92 g, 2.3 mmol), (1R,2R)-(+)-dipbenyl-ethylenediamine (0.50 g, 2.3 mmol) and manganese(II) acetate tetrahydrate (0.57 g, 2.3 mmol) were added at the name time in 500 mL of absolute ethanol under $N_2$. The reaction mixture was left stirring overnight at room temperature. Then bubble air through the solution for 4 h. After removal of solvent, the black oil obtained was dissolved in the minimum quantity of acetone and precipitated by adding a large quantity of bexane. The precipitate was then filtered off, washed several times with hexane and dried under vacuum 72 h, leading to a dark powder (1.7 g, 98% Yield).

Mass spectrometry, (ES-MS, MeOH) m/z =619.2 (M+); UV-visible (MeOH HPLC grade) λ($\epsilon mol^{-1}$ L $cm^{-1}$): 236 (51.1×10$^3$), 288 (15.3×10$^3$), 324 (13.5×10$^3$), 412 (5.2×10$^3$); Anal. Calcd for $C_{36}H_{35}N_2O_8Mn.3H_2O$: C, 59.02; H, 5.64; N, 3.82. Found: C, 58.76; H, 5.32; N, 3.72.

D. General Method For the Preparation of C151:

This example ilustrates a method that can be used to prepare C151, which is also referred to herein as FC-06-151.

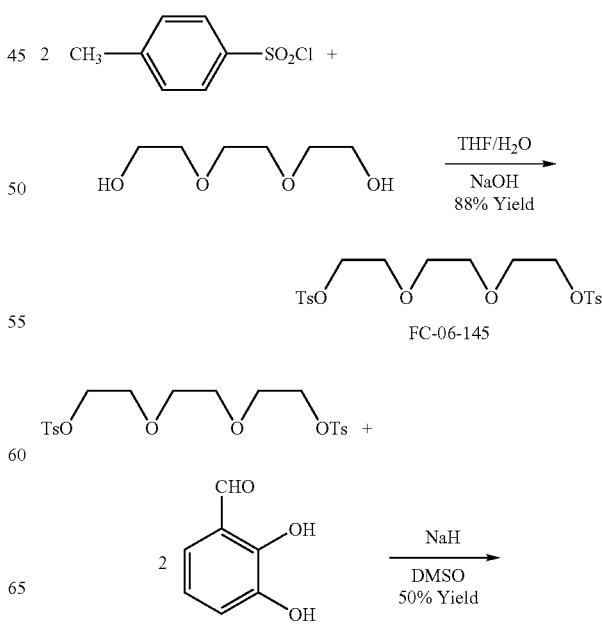

-continued

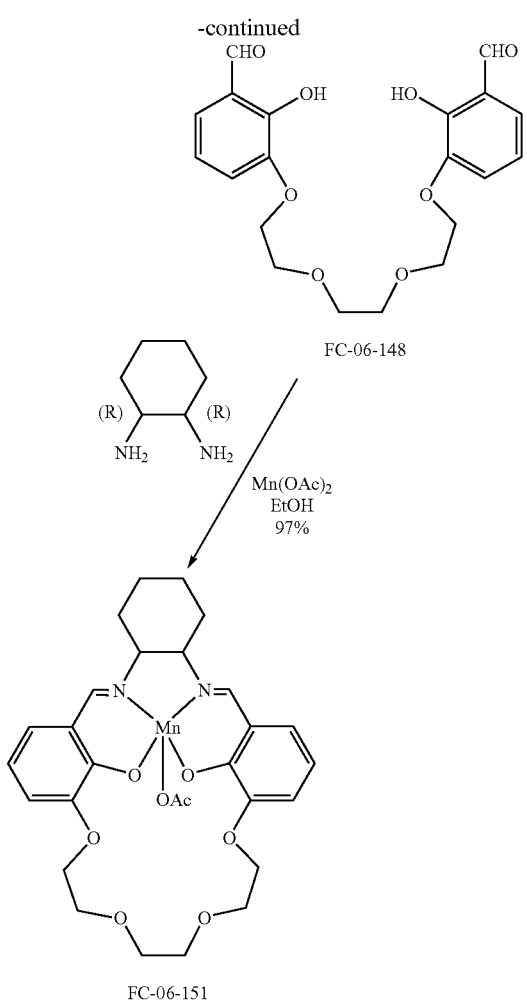

1. Experimental Procedure

General. All starting materials were obtained from Aldrich and used as received. All moisture-sensitive reactions were performed under an atmosphere of dry 5 nitrogen. Dry DMSO was obtained by distillation over 4A activated molecular sieves and keep on 4A activated molecular sieves.

2. II-I-Triethylene glycol ditoluene-4-sulfonate (FC-06-145)

The procedure used followed that set forth in Comforth, J.W., et al, *Tetrahedron*, 1973, 29, 1659–1667, the teachings of which are incorporated herein by reference.

A solution of toluene-4-sulfonyl chloride (84g) in THF (150 mL) was added in small portions with shaking, to a solution of tri-(ethylene glycol) (30g) and NaOH (21 g) in water (100 mL). The mixture was shaken for 2 h and left overnight. The product was extracted with toluene, the toluene extract washed with water, diluted $Na_2CO_3$ aq and water, dried ($CaCl_2$) and evaporate to dryness. The residue was crystallized from toluene/ether. The precipitate was filtrated, washed several times with ether, leading to a white powder (80.96 g, 88% Yield).

$^1$H NMR (CDCl$_3$) δ7.80 (d, J=8.4 Hz, 4H, HAr), 7.35 (d, J=8.4 Hz, 4H, HAr), 4.15 (m, 4H, TsOCH$_2$CH$_2$O), 3.66 (m, 4H, TsOCH$_2$CH$_2$O), 3.41 (S, 4H, OCH$_2$CH$_2$O), 2.46 (s, 6H, CH$_3$); mass spectrometry, (EI, 70 eV) m/z =286 (M-TsOH, 0.69%); Anal. Calcd for C$_{20}$H$_{26}$O$_8$S$_2$: C, 52.39; H, 5.72. Found: C, 52.67; H, 5.31.

3. II-2-3,3′-(3,6-Dioxaoctane-1,8-diyldioxy)bis(2-hydroxybenzaldehyde) (FC-06-148)

The procedure followed was set forth in Van Staveren, C. J., et al., *J. Am. Chem. Soc.* 1998, 110, 4994–5008, the teachings of which are incorporated by reference.

To a suspension of NaH (60% in oil) under N$_2$ (6.48 g, 0.16) in 35 mL of dry DMSO a solution of 2,3-dihydroxybenzaldehyde (10.18 g, 0.073 mol) in 40 mL of dry DMSO was added over a period of 2 h, under a vigorous stirring. The temperature was kept below 25° C. After stirring for 1 h (FC-06-145) (16.73 g, 0.036 mol) was added in one portion. This mixture was stirred 24 h at room temperature. Subsequently 300 mL of water was added, and this aqueous layer was acidified with 6M HCl to pH=1 and extracted with CHCl$_3$ (1L). Combined organic layers were dried over MgSO$_4$. After removal of solvent a crude product was obtained which was purified by column chromatography (CH$_2$Cl$_2$, iPrOH 2.5%). Layers containing the product with Rf=0.35 were combined and solvent were removed. MeOH was added to the sticky orange oil until the compound precipitated. The precipitate was filtered off and dried under vacuum, leading to a slightly yellow solid (6.3 g, 44% Yield).

$^1$H NMR (CDCl$_3$) δ10.88 (s, 2H, OH), 9.95 (s, 2H, CHO), 7.19 (m, 4H, HAr), 6.92 (m, 2H, HAr), 4.22 (t, J=5.1 Hz, 4H, ArOCH$_2$CH$_2$O), 3.90 (t, J=5.1 Hz, 4H, ArOCH$_2$CH$_2$O), 3.78 (s, 4H, OCH$_2$CH$_2$O); mass spectrometry, (EI, 70 eV) m/z=390 (M+, 18.47%); 1R (Nujol) 1637 (C=O) cm$^{-1}$; Anal. Calcd for C$_{20}$H$_{22}$O$_8$: C, 61.53; N, 5.68. Found: C, 60.67; H, 5.40.

4. II-3-EUK-500 (FC-06-151 or C151)

(FC-06-148) was previously crushed in order to obtain a very fine powder. (FC-06-148) (1.99 g, 5.1 mmol), (1R,2R)-(−)-diaminocyclohexane (0.58 g, 5.1 mmol) and manganese (II) acetate tetrahydrate (1.25 g. 5.1 mmol) were added at the same time in 500 mL of absolute ethanol under N$_2$. The reaction mixture was left stirring overnight at room temperature. Then bubble air through the solution for 4 h. After removal of solvent, the black oil obtained was dissolved in the minimum quantity of methanol and precipitated by adding a large quantity of diethylether. The precipitate was then filtred off, washed several times with diethylether and dried under vacuum 22 h, leading to a dark powder (2.5 g, 78% Yield).

Mass spectrometry, (ES-MS, MeOH) m/z=521.2 (M+); UV-visible (MeOH HPLC grade) λ(εmol$^{-1}$ L cm$^{-1}$): 232 (44.5×10$^3$), 292 (13.3×10$^3$), 320(12.0×10$^3$), 402 (5.1×10$^3$); Anal. Calcd for C$_{28}$H$_{33}$N$_2$O$_8$Mn.2.5H$_2$O: C, 53.76; H, 6.12 ; N, 4.47. Found: C, 53.95; H, 5.86; N, 4.32.

II. Example II

This example illustrates the various assays that can be used to screen the cyclic salen-metal compounds (CSMCs) of the present invention for biological activity. In addition, suitable assays for screening the cyclic salen-metal compounds of the present invention for biological acitivity are also disclosed in U.S. Pat. Nos. 5,403,834, 5,834,509, 5,696, 109 and 5,827,880, the teachings of which are incorporated herein by reference for all purposes.

A. Assays for Screening for Catalytic Activities

The following assays can be used to screen for antioxidant catalytic activity. More particularly, the following assays can be used to screen for superoxide dismutase and catalase activities.

The SOD activity of the compounds can be determined by evaluating the inhibition of the reduction of cytochrome c produced by the oxygen free radical generating system, xanthine plus xanthine oxidase. Cytochrome c reduction is monitored spectrophotometrically at 550 nm according to the method described in Darr, et al. (1987) *Arch. Biochem. Biophys.* 258:351, incorporated herein by reference. The concentration of xanthine oxidase is adjusted such that it produces a rate of reduction of cytochrome c at 550 nm of 0.025 absorbance unit per minute. Under these conditions, the amount of SOD activity required to inhibit the rate of cytochrome c reduction by 50 percent (i.e., to a rate of 0.0125 absorbance unit per minute) is defined as one unit of activity. Cyclic salen-metal complexes are identified as antioxidants if they have at least 0.1 unit of activity at a concentration of 1 mM under these standard assay conditions.

Catalase activity can be measured using a spectrophotometric method in which the decomposition of hydrogen peroxide is monitored at 240 nm according to the method of Aebi, et al. (1984) *Methods Enzymol.* 105:121, incorporated herein by reference. One unit of catalase activity is defined as the amount of enzyme (or salen-metal complex) required to decompose 1 μmole of hydrogen peroxide per minute.

Each of the compounds to be tested is formulated in water or saline, wherein the compounds are stable, i.e., no loss of activity observed after several weeks of storage at room temperature. Frequently, it is desirable to first dissolve the cyclic salen-metal complex in an organic solvent (e.g., ethanol) and then dilute the solution into a more polar solvent such as water. This is particularly preferred for salen-metal species that are relatively hydrophobic.

B. Assays for Screening for In Vivo Biological Activity in Brain Ischemia

Using the following assay, the CSMCs of the present invention can be readily screened to determine their therapeutic potential in brain ischemia (stroke).

A widely used assay to determine the therapeutic potential of cyclic salen-metal compounds in brain ischemia (stroke) consists of evaluating their ability to prevent irreversible damage induced by an anoxic episode in brain slices maintained under physiological conditions. Rat brain slices are maintained at 35° C. in an interface chamber in an artificial cerebrospinal fluid containing: 124 mM NaCl, 3 mM KCl, 1.25 mM $KH_2PO_4$, 3 mM CaCl, 1 mM $MgCl_2$, 26 mM $NaHCO_3$, 10 mM D-glucose, and 2 mM L-ascorbate, continuously gassed with a mixture of $O_2:CO_2$ (95:5). The atmosphere of the chamber is also continuously gassed with the mixture of $O_2:CO_2$ (95:5), except during the anoxic episode when it is replaced by $N_2$. Axons are electrically stimulated and the evoked excitatory post-synaptic potentials (EPSPs) are recorded using microelectrodes.

Typically, the EPSPs are recorded under normal conditions, five minutes following replacement of $O_2$ with $N_2$ (ischemic episode), and 30 to 40 minutes following reoxygenation. The extent of permanent damage can be quantified by measuring both the amplitude (in mV) and the initial slope (in mV/msec) of the EPSP. More particularly, brain slices are incubated in the absence or presence of 50 μM a cyclic salen-metal compound (CSMC) and subjected to an episode of ischemia/reoxygenation. After 5 minutes of baseline recording, $O_2$ is replaced by $N_2$ for an average of 5 minutes. $O_2$ is then reintroduced and recording is continued for another 50 minutes. As an additional assessment of efficacy, the percentage of viable slices following repeated ischemic episodes can be evaluated. A slice is considered viable if an EPSP of 3 mV amplitude could be elicited by increasing stimulation intensity.

C. Assays for Testing in Animal Model of Parkinson's Disease

Using the following assay, the CSMCs of the present invention can be readily screened to determine their therapeutic potential in treating Parkinson's disease.

An animal model of Parkinson's disease involving iatrogenic hydroxyl radical generation by MPTP (Chiueh, et al. (1992) *Synapse* 11:346, incorporated herein by reference) can be used to evaluate the protective effect of cyclic salen-metal compounds of the present invention on free radical-induced damage. The neurotoxin, MTP, has been shown to lead to the degeneration of dopaminergic neurons in the brain, thus providing a good model of experimentally induced Parkinson's disease (e.g., iatrogenic toxicity). This model is now widely accepted in the art and is used for evaluating potential therapeutic agents for this disease.

The number of dopaminergic neurons in brains of mice treated with either: (1) MPTP alone, (2) the antioxidant cyclic salen-metal complex (CSMC), (3) pretreatment with CSMC and then MPTP, or (4) untreated controls, are assayed by measurement of the binding of the dopamine reuptake ligand, mazindol. Tritiated mazindol is used for binding studies on samples of the globus pallidus, caudate nucleus, and striatum of mouse brain according to conventional methods; specific binding of tritiated mazindol is determined autoradiographically or by membrane binding (specific binding to the membrane fraction). The experiment is typically performed over a 7 day period. Mice in the MPTP group are treated intraperitoneally with MPTP alone (40 mg/kg each day on days 1 and 2). Mice in the MPTP+CSMC group are pretreated with CSMC (33 mg/kg, i.p.) immediately prior to MPTP on days 1 and 2, and are given CSMC (33 mg/kg) alone on day 3. The animals are sacrificed after 7 days and the results analyzed.

D. Assays for Screening for the Ability to Protect Against Ischemia and Reperfusion Using the following assays, the CSMCs of the present invention can be evaluated for their ability to protect hearts from ischemia/reoxygenation damage, both functionally and structurally.

Rats are given an intramuscular injection of 0.25 ml of an iron-dextran solution (100 g iron hydroxide, 99 g dextran, water up to 1 L) every third day during a 5-week period to achieve a significant iron overload in cardiac tissue. At the end of this treatment, rats are anesthetized with sodium pentobarbital (40 mg/kg) and heparin (1,000 IU/kg) is administered via a femoral vein. Hearts are then removed and rapidly perfused through the aorta according to the technique described by Langendorff, O., (1895) *Pflügers Arch.* 61:291, at a constant flow rate of 11 ml/minute. The perfusion fluid is a modified Krebs-Henseleit buffer containing (in mmol/l): NaCl 118, KCl 5.9, $NaHCO_3$ 25, $MgCl_2$ 1.2, $NaH_2PO_4$ 0.6, $CaCl_2$ 2.4, Glucose 11. The pH is maintained at about 7.4±0.05 when the perfusion medium is saturated with $O_2$—$CO_2$ (95%–5%) at 37° C. The perfusion apparatus is fully thermostated such that the temperature of the perfusion medium is about 37.0±0.5° C. when it reaches the aorta. An ultra-thin balloon is inserted in the left ventricle immediately after the initiation of aortic perfusion and is inflated so as to obtain an end-diastolic pressure of 5 mm Hg. A 15 minute stabilization period is initiated immediately following balloon placement. At the end of this period, systolic and diastolic ventricular pressures and heart beat rate (HR) are recorded through a pressure transducer linked to the ventricular balloon. Left Ventricular Developed Pressure (LVDP) is calculated by the difference between systolic and diastolic pressure and the product HR×LVDP is taken as an index of oxygen consumption. Hearts are then subjected to a 15 minute total global normothermic ischemia, followed by 15 minutes of reperfusion with the perfusion medium used initially. During this 15 minute reperfusion, heart rate, and diastolic and systolic pressures are monitored. Early ventricular fibrillations are analyzed 1 min. after the start of the reperfusion.

Three experimental groups are typically studied. Group 1 in which hearts are perfused with the standard perfusion fluid (control group); group 2 in which hearts are perfused in the presence of dimethylthiourea (DMTU, 10 mM; group 3 in which hearts are perfused in the presence of the CSMC of the present invention (50 µM). Heart rates (HR), systolic pressures (SP), diastolic pressures (DP), and the products HR×LVDP, in the three experimental groups, are determined after 15 minutes of perfusion, before ischemia, 1 minute after reperfusion and 15 minutes after reperfusion. The number of hearts exhibiting episodes of ventricular fibrillation 1 minute after reperfusion is also determined.

After the 15 minute reperfusion, 3 hearts in each group are prepared for electron microscopy by perfusion with 2.5% glutaraldehyde. Ultra-thin slices (500–600 Å thickness) are examined. Mitochondria and sarcomeres are evaluated. Mitochondria are classified into Type A (normal), Type B (swollen, unbroken), and Type C(ruptured membranes). Sarcomeres are classified into Type A (normal) and Type B (contacted and/or necrosis).

E. Assays for Screening for the Ability to Prevent the Development of Symptomatic EAE Using the following assay, the CSMCs of the present invention can be readily screened for their ability to prevent the development of symptomatic EAE.

Experimental Autoimmune Encephalomyelitis (RAE) is an animal model of multiple sclerosis. Typically, 30 SJL female mice, aged 10 weeks, are divided into 2 groups of 20 mice (control) and 10 mice (CSMC treated)

Mice in both groups are immunized with an encephalitogenic PLP peptide in complete Freund's adjuvant subcutaneously, followed by Pertussis Toxin (IV). Pertussis toxin is repeated on day 3 post immunization.

Mice in the CSMC group are treated daily (1 mg/mouse, approximately 40 mg/kg) by IP injection, starting from 2 days prior to immunization through day 14 after immunization. Animals are analyzed to determine if they developed symptomatic EAR and are scored as follows:

| Stage I: | Limp tail syndrome |
| Stage II: | Hind leg paralysis |
| Stage III: | Hind leg paralysis-Dragging movement |
| Stage IV: | Paralytic immobility, weight loss |

F. Assays for Screening for the Ability to Treat Actute Lung Injury (ALI)

Using the following assay, the CSMCs of the present invention can be readily screened for their ability to treat endotoxin-induced, e.g., sepsis-induced, ALI in humans.

Reactive oxygen metabolites (ROM's) are important mediators of acute lung injury (ALI) in sepsis and endotoxemia. When treatment with CSMCs of the present invention is begun prior to lipopolysaccharide (LPS; endotoxin) infusion, such agents can prevent many of the manifestations of LPS-induced ALI in pigs. Treatment with CSMC after LPS administration can be used to determine if the CSMC affords protection against endotoxin-induced ALI in pigs.

All pigs are pre-treated at T=−18 h with *Escherichia coli* 0111:B4 LPS (20 µ/kg). Pigs in the Ringer's lactate (RL) group receive no further treatment. From T=0 to 60 min, pigs in both the LPS and LPS/CSMC groups are challenged with LPS (250 µ/g). Immediately following the completion of LPS infusion, beginning at T=−60 min, pigs in the LPS/C7 group receive a bolus dose of CSMC (10 mg/kg in 5% dextrose) followed by a continuous infusion (e.g., 10 mg/kg-h). Various physiological parameters reflecting lung function are monitored (Gonzalez, et al. (1995) *J. Pharm. Exp. Ther.* 275:798). Lung wet-to-dry weight ratio is determined post-mortem. Lung lipid peroxidation is estimated fluorometrically by measuring thiobarbituric acid reactive products in the lipid fraction of lung parenchymal tissue harvested at T=300 min.

G. Assays for Screening for the Ability to Prevent Lipid Peroxidation Induced By Acidosis Using the following assay, the CSMCs of the present invention can be readily be screened for their ability to prevent lipid peroxidation induced by acidosis. Acidosis is known to induce extensive oxidative damage. Lipid peroxidation is a consequence of such oxidative damage and has been found to be associated with a number of human pathologies.

Hippocampal slices (400 µm thick) can be obtained from Sprague-Dawley rats (150–200 g) and collected in preoxygenated (95% $O_2$/5% $CO_2$) Krebs-Ringer phosphate medium (pH 7.4) containing NaCl 120 mM, KCl 5 mM, $CaCl_2$ 1.3 mM, $MgCl_2$ 1.2 mM, NaPhosphate 16 mM (pH 7.4) and glucose 10 mM. After 15 minutes preincubation in a water bath at 35° C. under agitation, the buffer is replaced with the same buffer (control) or a modified buffer (lactate buffer) containing NaCl 90 mM, KCl 5 mM, $CaCl_2$ 1.3 mM, $MgCl_2$ 1.2 mM, Na Phosphate 16 mM and lactic acid 30 mM (pH 5.0). When present, the cyclic salen-metal complex (50 µM) is added during the preincubation and the incubation periods. After 100 minutes, slices are collected and homogenized in 0.9 ml of TCA 5%, whereas 0.35 ml of TCA 5% is added to 0.5 ml of the incubation medium. Lipid peroxidation is measured by adding 0.25 ml of a thiobarbituric acid reagent (TBAR) to 0.85 ml of the TCA extracts and incubating the mixture for 60 minutes at 85–93° C. Lipids are then extracted with 2×0.5 ml 1-butanol by vortexing for 10 seconds, then centrifuging at 2,000 rpm for 10 minutes. The absorbance of peroxidized lipids in the alcohol phase is measured in a spectrophotometer at 532 nm. Data are expressed as nmoles of malondialdehyde (MDA) using authentic MDA to establish a standard curve. Proteins are measured from an aliquot of the TCA extracts using the method of Bradford (*Anal. Biochem.*, 72:248–254 (1976)), and the final results are calculated as nmoles MDA formed/mg protein.

H. Assays for Screening for the Ability to Protect Against Neuronal Injury

6-OHDA in mice. Adult male CFW mice are anesthetized with ketamine and rompum, and immobilized in a stereotaxic device. 6-OHDA, as the hydrobromide salt, is dissolved in normal saline with 1% ascorbate, and 50 µg is administered in lateral ventricle by means of a 10 µl Hamilton syringe. The CSMC of the present invention (66 mg/kg, i.p.) is administered daily for 4 days. Animals are sacrificed about 7 days later, and neuronal pathology is assessed by measuring $^3$H-mazindol binding in striatal homogenates.

Using the foregoing assay, the CSMCs of the present invention can be readily be screened for their ability to prevent against 6-OHDA-induced neuronal injury, i.e., 6-OHDA-induced loss of nigrostriatal dopaminergic neurons.

I. Assays for Screening for Peroxidase Activity

Using the following assays, the CSMCs of the present invention can be screened for peroxidase activity.

Peroxidase activity can be assayed by monitoring the hydrogen peroxide-dependent oxidation of 2,2'-azino-bis(3-ethylbenzthiazoline-6) sulfonic acid (ABTS) spectrophotometrically. Standard assay mixtures consist of 50 mM sodium phosphate, pH 8.1, 0.9% sodium chloride, 0.5 mM ABTS, and $H_2O_2$ and the CSMC of the present invention. In certain embodiments, 50 mM sodium phosphate buffers of pH 6.0 or pH 7.1 can be substituted. Assays are conducted at about 27±0.2° C. ABTS oxidation is monitored at 740 or 500 nm to eliminate interference by the CSMC, many of which absorb in the vicinity of the $\lambda_{max}$ of oxidized ABTS, and to avoid absorbance values that exceeded the linear range of the spectrophotometer. The amount of oxidized ABTS is estimated using an $\Delta\epsilon_{740}$ of 20,300 $M^{-1}cm^1$ or an of $\Delta\epsilon_{500}$ 3400 $M^{-1}$ $cm^1$ calculated based upon the published molar extinction coefficient at 405 nm (36,800).

J. Assays for Screening for Cell Protection

Using the following assay, the CSMCs of the present invention can be readily screened for their ability to protect cells against glucose and glucose oxidase, a hydrogen peroxide-generating system.

Human dermal fibroblasts (American Type Culture Collection) were grown to confluence on 96-well plates in culture medium consisting of Dulbecco's modified Eagle's medium (4.5 g of glucose/liter) with 10% calf serum and antibiotics. To induce oxidative toxicity, cells were incubated with culture medium containing 0.02 unit/ml glucose oxidase for 18 hr in the presence or absence of test substances (either salen-manganese complex or bovine liver catalase), as indicated in the figure legend. After the incubation period, cell layers were washed with phosphate-buffered saline and fresh medium lacking glucose oxidase, and test substances were added. Cell viability was then assessed using the XTT reagent according to the manufacturer's instructions, with absorbance read at 490 mn with a microplate reader (model 3550, BioRad, Hercules, Calif.). Cell viability was also confirmed by visual inspection of the monolayers under a phase contrast microscope. Salen-manganese complexes, used under these conditions, did not interfere with XTT-associated color development.

III. Example III

This example illustrates a mouse model that can be used to screen for delayed hypersensitivity (DTH).

Mice were pre-sensitized with 3% oxazolone on the abdomen and on day 8, challenged with 1.7% oxazolone topically on one ear to induce an inflammatory edema. C113 or ethanol, i.e., the vehicle control, was applied topically to the ear immediately after the oxazolone challenge. The ear edema is measured by comparing the tissue water content (the wet weight minus the dry weight) of the challenged car to that of the control ear. The percent edema (% water in the right/left ear) in the vehicle control was 8.1% and 4.6% for a C113 dose of 27 nmoles/ear.

IV. Example IV

This example illustrates an example of a topical formulation comprising a salen-metal compound of the present invention. All percentages and ratios herein are by weight, unless otherwise specified. An exemplar moisturizing lotion can be prepared by combining the following components utilizing conventional mixing techniques.

| Components | Percent by Weight of Composition |
|---|---|
| Water (purified) | 70.94 |
| Carbomer viscosity control agents (commercially available in the Acritamer series from R.I.T.A. Corp.) | 0.23 |
| Alkyl Parabens | 0.90 |
| Glycerin | 3.50 |
| Potassium Hydroxide | 0.09–0.15 |
| Cetyl Alcohol | 1.25 |
| Stearic Acid | 0.75 |
| Glyceryl Stearate | 0.63 |
| Polyoxyethylene Stearyl Alcohol (commercially available in the Brij series from ICI Americas, Inc.) | 1.75 |
| Coco Caprylate/caprate | 2.00 |
| C12–C15 Alcohol Benzoate (Finsolv TN-commercially available from Finetex, Inc.) | 2.00 |
| Cyclic Salen-Metal Compound | 2.00 |
| Octyl Methoxycinnamate | 7.50 |
| Benzophenone-3 | 1.00 |
| Octyl Dimethyl PABA | 1.00 |
| Dimethicone | 0.30 |
| Imidazolidinyl Urea | 0.10 |
| Ethylene Acrylate Copolymer | 3.80 |
| Tyros me | 0.10 |

This lotion may be topically applied to inhibit damage caused by acute or chronic UV exposure. Use of an amount of lotion sufficient to deposit about 0.1 to 100 μg/cm² of the CSMC of the present invention to the skin immediately prior to UV exposure is appropriate. Substantially similar results are obtained if the lotion is applied to the skin up to 4 hours prior to UV exposure or up to 30 minutes after UV exposure. Substantially similar results are obtained if the octyl methoxycinnamate, benzophenone-3, and octyl dimethyl PABA are replaced, in whole or in part, with 2-ethylhexyl p-methoxycinnamate, butylmethoxydibenzoylmethane, 2-hydroxy-4-methoxybenzophenone, and mixtures thereof.

A skin lotion is prepared by combining the following components utilizing conventional mixing techniques.

| Components | Percent by Weight of Composition |
|---|---|
| 4-N,N-(2-Ethylhexyl) methylamino-Benzoic Acid Ester of 4-(2-Hydroxyethoxy)-Dibenzoyl Methane | 10.00 |
| Water (purified) | 47.54 |
| Dimethyl Isosorbide | 8.00 |
| Dioctyl Maleate | 8.00 |
| C12–15 Alcohol Benzoate (Finsolv TN-commercially available from Finetex, Inc.) | 8.00 |
| Glycerin | 3.50 |
| Ethylene Acrylate Copolymer | 3.80 |
| Antioxidant salen-metal compound (e.g., C7) | 2.00 |
| Cetyl Alcohol | 1.75 |
| Polyoxyethylene Stearyl Alcohol (commercially available in the Brij series from ICI Americas, Inc.) | 1.75 |
| Stearic Acid | 1.25 |
| Glyceryl Stearate | 1.13 |
| Alkyl Parabens | 0.90 |
| Titanium Dioxide | 0.90 |
| Dimethicone | 0.30 |
| Carbomer viscosity control agents (commercially available in the Acritamer series from R.I.T.A. Corp.) | 0.23 |
| Imidazolidinyl Urea | 0.10 |
| Potassium Hydroxide | 0.15 |
| Tyrosine | 0.10 |

This lotion is useful for topical application to inhibit damage caused by acute or chronic UV exposure or exposure to an oxyradical environment. Use of an amount of lotion sufficient to deposit about 0.1–100 μg/cm² of the antioxidant CSMC of the present invention to the skin immediately prior to UV exposure is appropriate. Substantially similar results are obtained if the lotion is applied to the skin up 4 hours prior to UV exposure or up to 30 minutes after UV exposure.

V. Example V

This example illustrates the stability of exemplar cyclic salen-metal compounds of the present invention in both rat plasma and acid.

A. Stability of Cyclic Salen-Manganese Complexes in Rat Plasma

Each compound (12–16 μM) was incubated in rat plasma diluted 3-fold in water at 37° C. Aliquots were withdrawn ($T_1$ aliquot was withdrawn as rapidly as possible, ~20–30 sec after mixing), extracted with methanol-1% trichloroacetic acid, and extracts were analyzed by HPLC for parent compound.

| Compound | Time (min) | % remaining (% $T_1$) |
|---|---|---|
| noncyclic reference | 20 | 60 |
|  | 128 | 6 |
| C117 | 20 | 100 |
|  | 128 | 89 |
| C113 | 20 | 75 |
|  | 128 | 42 |

B. Stability of Cyclic Salen-Managanese Complexes in Acid

Each compound (50 to 100 μM) was incubated in 1 M HCl for 24 hr. Amount of compound remaining was determined spectrophotometrically.

| Compound | % remaining after 24 hr |
|---|---|
| non-cyclic reference | <6 |
| C101 | 78 |
| C113 | 26 |

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purposes.

What is claimed is:

1. A salen-metal compound, wherein said salen-metal compound is selected from the group consisting of:

C101:

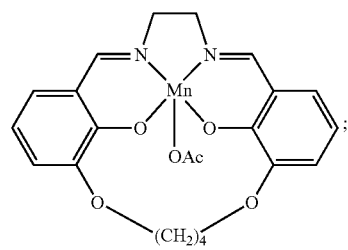

C102:

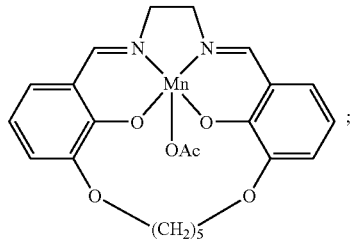

C103:

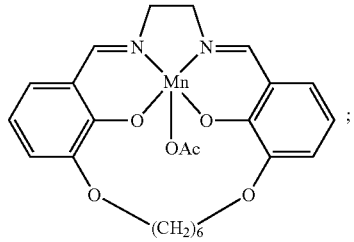

C104:

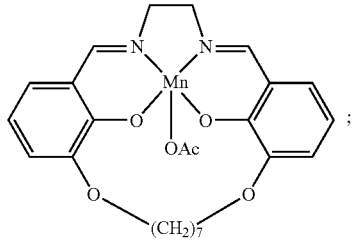

C105:

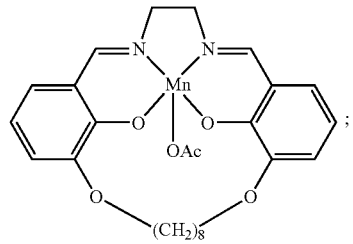

C106:
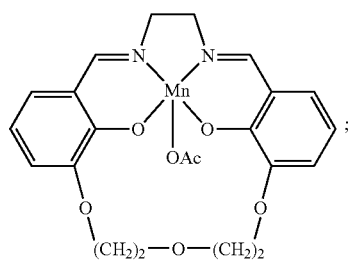
C107:
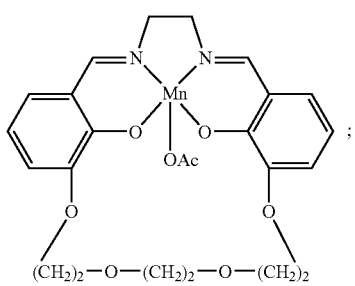
C108:
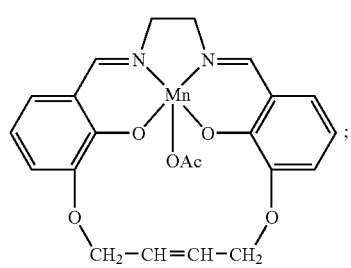
C109:
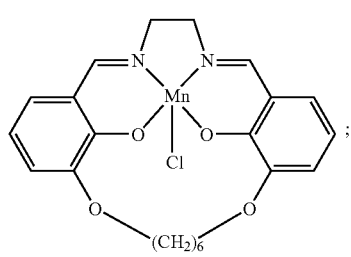
C110:
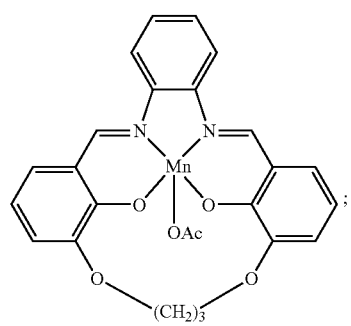
C111:
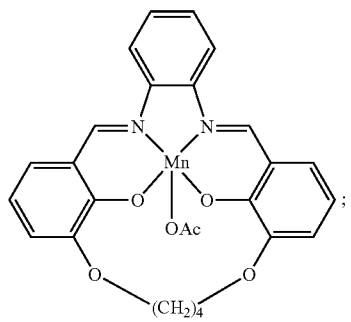
C112:
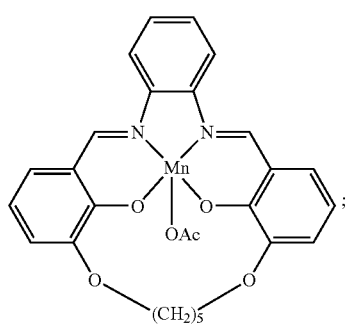
C113:
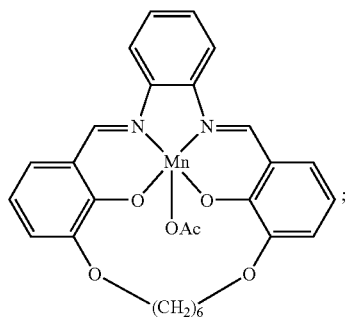
C114:
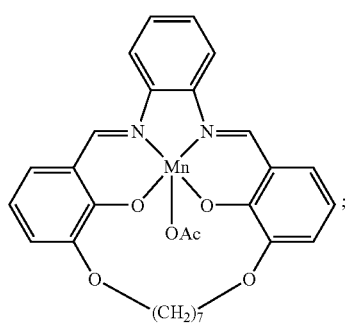

C115:
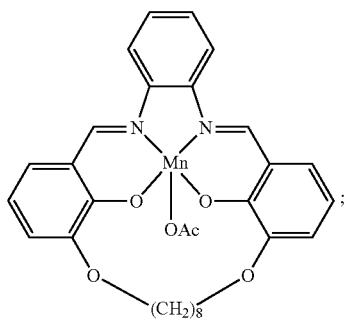
C116:
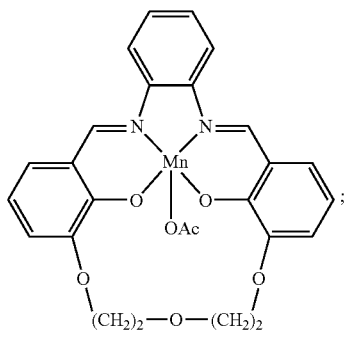
C117:
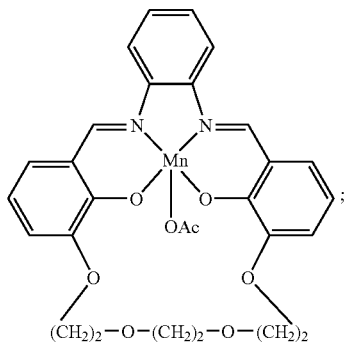
C118:
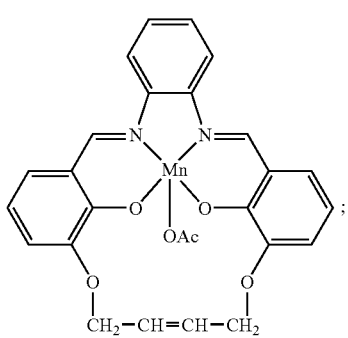
C119:
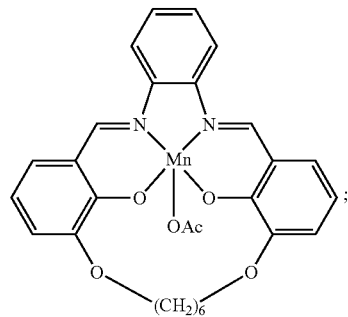
C120:
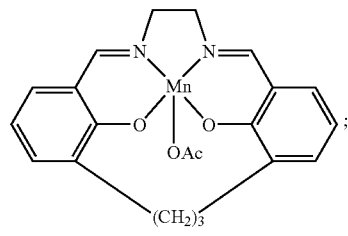
C121:
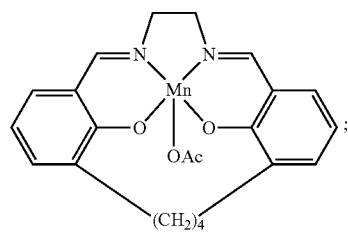
C122:
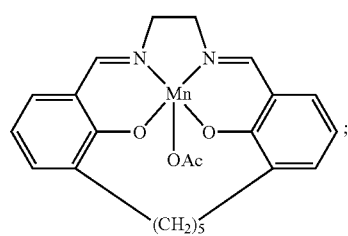
C123:
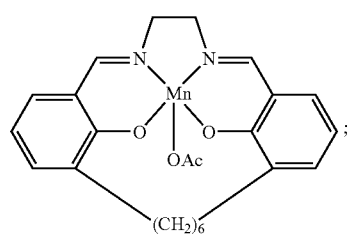

C124:
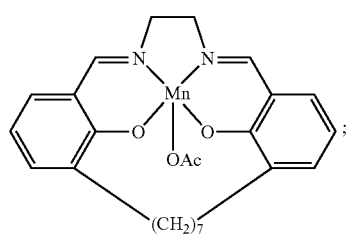
C125:
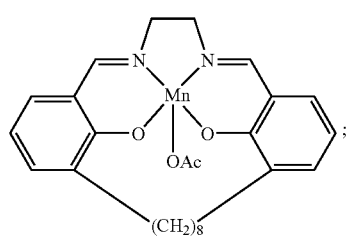
C126:
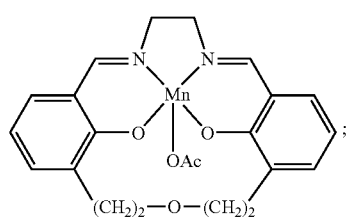
C127:
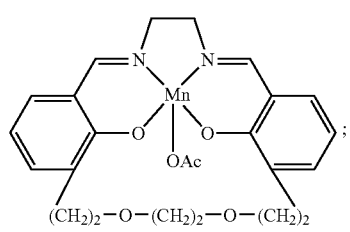
C128:
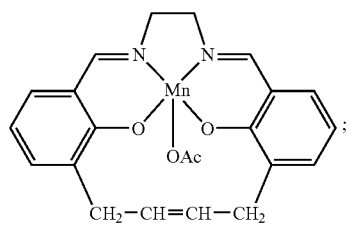
C129:
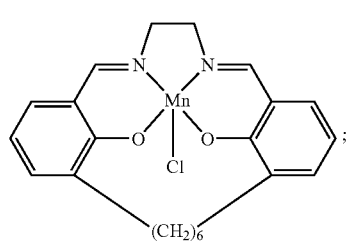
C130:
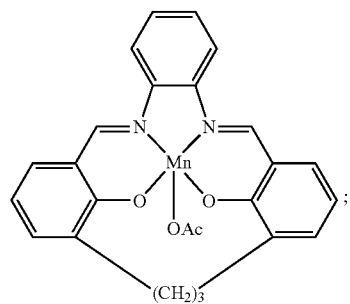
C131:
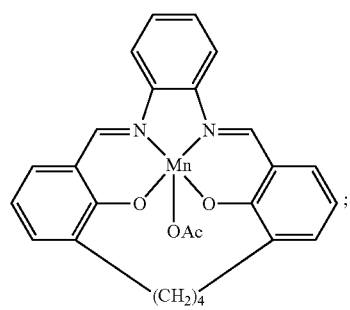
C132:
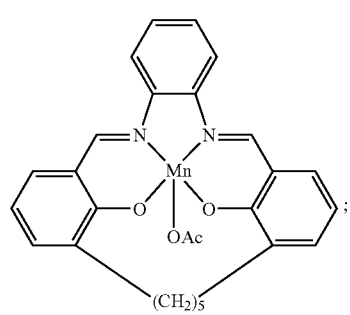
C133:
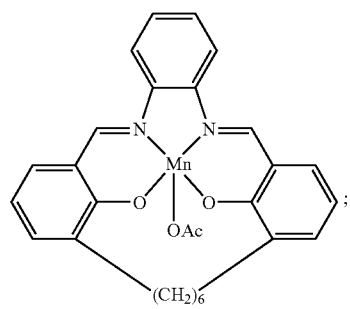

C134:

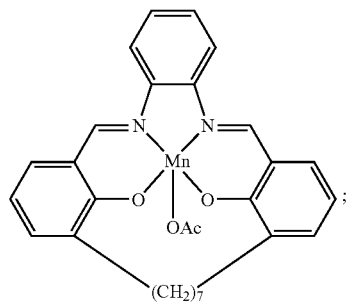

C135:

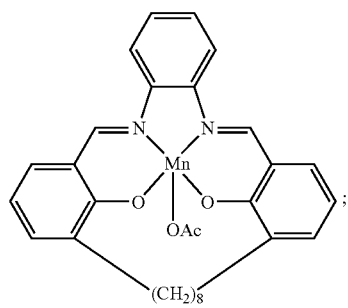

C136:

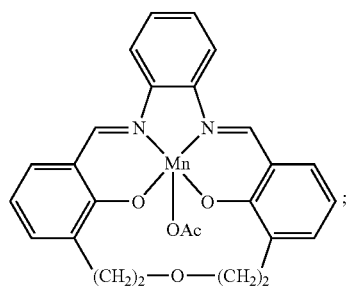

C137:

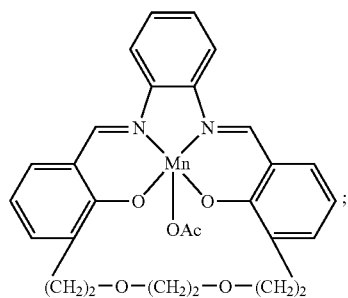

C138:

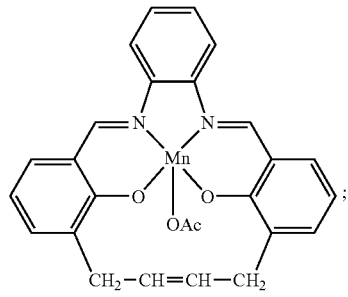

C139:

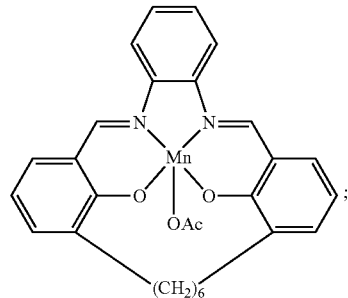

C151:

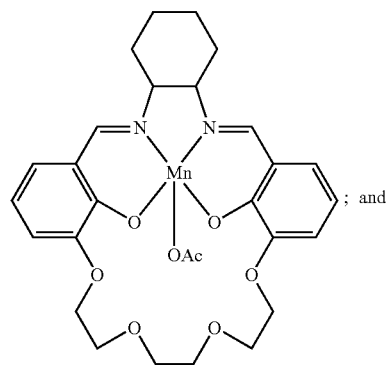

; and

C155

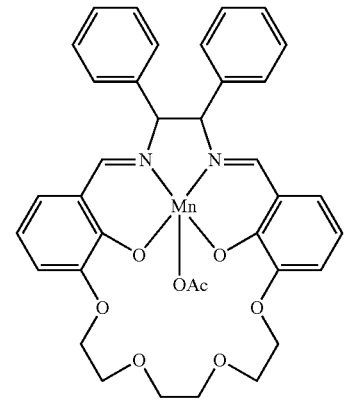

2. A pharmaceutical composition comprising a salen-metal compound of claim 1 and a pharmaceutically acceptable carrier, excipient or adjuvant.

3. The pharmaceutical composition in accordance with claim 2, wherein said pharmaceutical composition comprises an antioxidant amount of said salen-metal compound.

4. The pharmaceutical composition of claim 2, wherein said salen-metal compound is present in an amount such that said pharmaceutical composition superoxide dismutase activity and/or catalase activity in an aqueous solution.

5. A salen-metal compound in accordance with claim 1 having superoxide dismutase activity.

6. A salen-metal compound in accordance with claim 1 having catalase activity.

7. A salen-metal compound in accordance with claim 1 having peroxidase activity.

8. A salen-metal compound in accordance with claim 1 having catalase activity and peroxidase activity.

9. A salen-metal compound in accordance with claim 1 having superoxide dismutase activity, catalase activity and peroxidase activity.

10. A method for inhibiting damage to cells induced by reactive oxygen species, said method comprising contacting said cells with an antioxidant salen-metal compound of claim 1.

11. The method in accordance with claim 10, wherein said cells are blood cells.

12. The method in accordance with claim 10, wherein said cells are present in an excised organ.

13. The method in accordance with claim 12, wherein said excised organ is a member selected from the group consisting of heart, kidney, pancreas, liver, lung, skin, cornea and vasculature.

14. A composition comprising a topical carrier and a salen-metal compound of claim 1.

15. The salen-metal compound in accordance with claim 1, wherein said salen-metal compound is selected from the group consisting of:

C103:

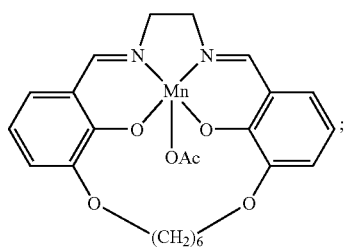

C105:

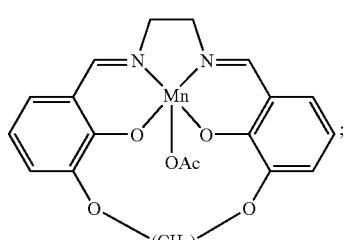

C106:

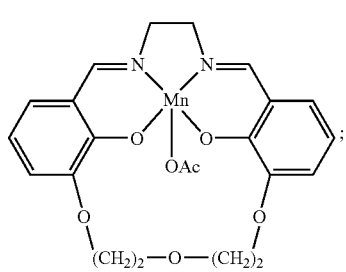

C107:

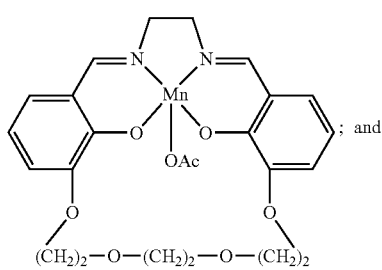
; and

C117:

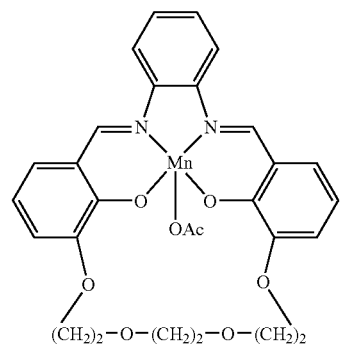

wherein OAc is acetate.

16. The method according to claim 10, wherein said salen-metal compound is selected from the group consisting of:

C103:

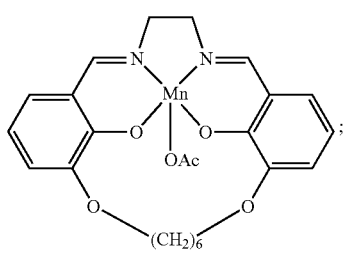

C105:

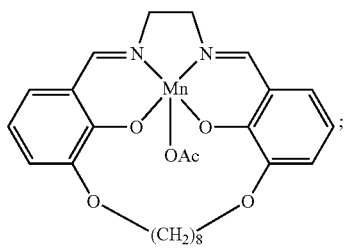

C106:

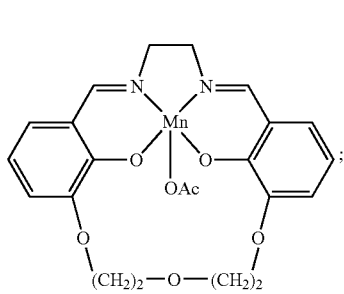

-continued

C107:

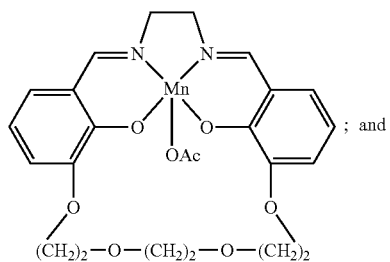
; and

C117:

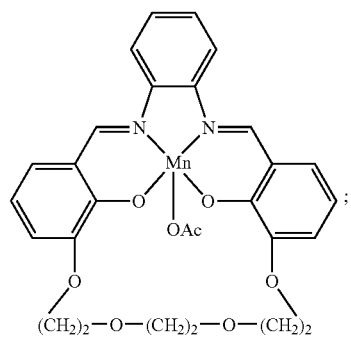
;

wherein OAc is acetate.

17. The salen-metal compound in accordance with claim 1, wherein said salen-metal compound is

C103:

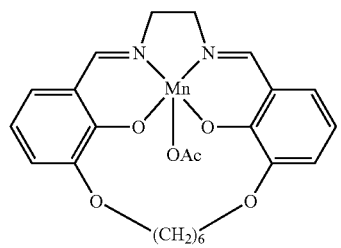

wherein OAc is acetate.

18. The salen-metal compound in accordance with claim 1, wherein said salen-metal compound is

C105:

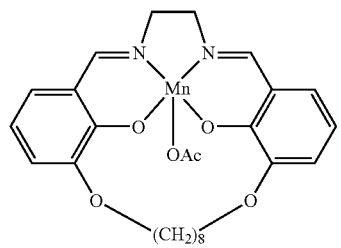

wherein OAc is acetate.

19. The salen-metal compound in accordance with claim 1, wherein said salen-metal compound is

C106:

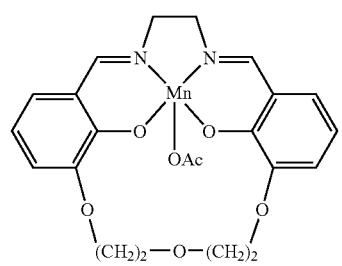

wherein OAc is acetate.

20. The salen-metal compound in accordance with claim 1, wherein said salen-metal compound is

C107:

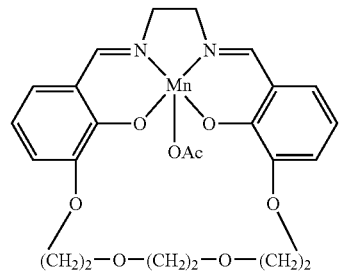

wherein OAc is acetate.

21. The salen-metal compound in accordance with claim 1, wherein said salen-metal compound is

C117:

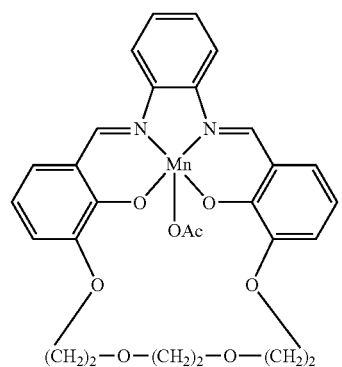

wherein OAc is acetate.

22. The method according to claim 10, wherein said salen-metal compound is:

C103:

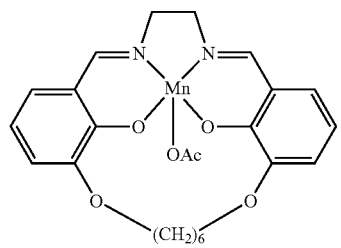

wherein OAc is acetate.

23. The method according to claim 10, wherein said salen-metal compound is:

C105:

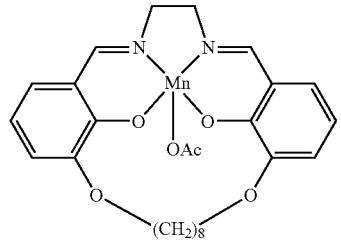

wherein OAc is acetate.

24. The method according to claim 10, wherein said salen-metal compound is:

C106:

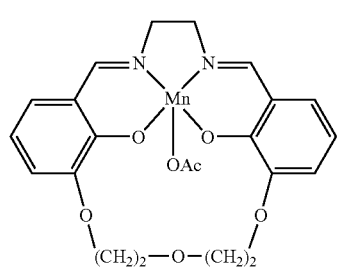

wherein OAc is acetate.

25. The method according to claim 10, wherein said salen-metal compound is:

C107:

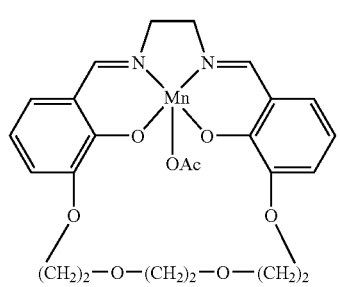

wherein OAc is acetate.

26. The method according to claim 10, wherein said salen-metal compound is:

C117:

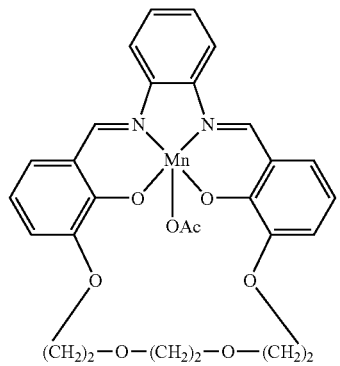

wherein OAc is acetate.

* * * * *

UNITED STATES PATENT AND TRADEMARK OFFICE
CERTIFICATE OF CORRECTION

PATENT NO.         : 7,122,537 B2
APPLICATION NO. : 10/432752
DATED                  : October 17, 2006
INVENTOR(S)       : Bernard Malfroy-Camine et al.

It is certified that error appears in the above-identified patent and that said Letters Patent is hereby corrected as shown below:

In The Claims:

• Column 50, line 13: Delete " C119: 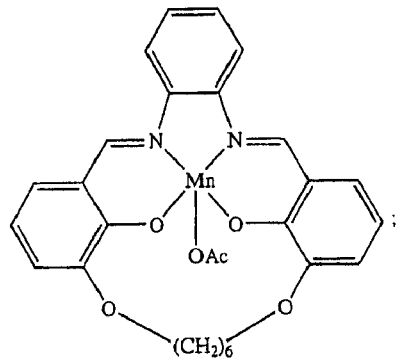 "

and replace with --C119: 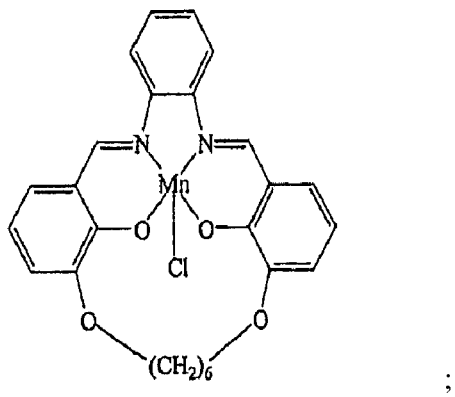 --

UNITED STATES PATENT AND TRADEMARK OFFICE
CERTIFICATE OF CORRECTION

PATENT NO. : 7,122,537 B2
APPLICATION NO. : 10/432752
DATED : October 17, 2006
INVENTOR(S) : Bernard Malfroy-Camine et al.

It is certified that error appears in the above-identified patent and that said Letters Patent is hereby corrected as shown below:

Column 54, line 12: Delete " C139: 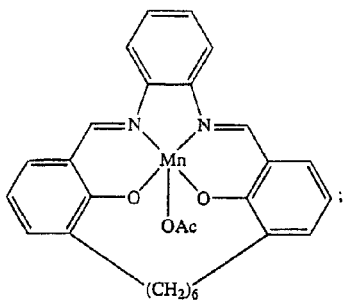 "

and replace with --. C139: 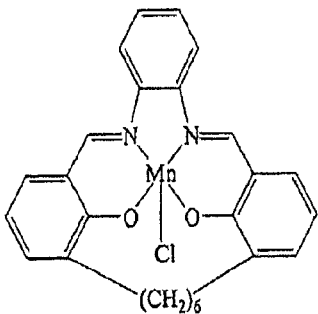 --

Signed and Sealed this

Thirteenth Day of May, 2008

JON W. DUDAS
*Director of the United States Patent and Trademark Office*